United States Patent
Lin et al.

(10) Patent No.: US 12,426,142 B2
(45) Date of Patent: Sep. 23, 2025

(54) INTELLIGENT HUMAN CENTRIC LIGHTING SYSTEM WITH AMBIENT LIGHT MONITORING OF LIGHTING SITE ENVIRONMENT

(71) Applicant: Lawrence Lin, Taoyuan (TW)

(72) Inventors: Lawrence Lin, Taoyuan (TW); Chih Hung Chang, New Taipei (TW)

(73) Assignee: Lawrence Lin, Taoyuan (TW)

( * ) Notice: Subject to any disclaimer, the term of this patent is extended or adjusted under 35 U.S.C. 154(b) by 188 days.

(21) Appl. No.: 18/320,005

(22) Filed: May 18, 2023

(65) Prior Publication Data
US 2023/0380038 A1 Nov. 23, 2023

Related U.S. Application Data

(60) Provisional application No. 63/343,717, filed on May 19, 2022.

(51) Int. Cl.
*H05B 47/11* (2020.01)
*A61M 21/00* (2006.01)
(Continued)

(52) U.S. Cl.
CPC .............. *H05B 47/11* (2020.01); *A61M 21/02* (2013.01); *H05B 45/12* (2020.01); *H05B 45/14* (2020.01);
(Continued)

(58) Field of Classification Search
CPC ........ H05B 47/11; H05B 45/12; H05B 45/14; H05B 45/325; H05B 47/19; H05B 47/196; H05B 47/1965; H05B 47/1985; A61M 21/02; A61M 2021/0044; A61M 2205/3306; A61M 2205/3553; A61M 2205/3584; A61M 2205/587;
(Continued)

(56) References Cited

U.S. PATENT DOCUMENTS

2021/0112647 A1* 4/2021 Coleman ................ H05B 47/16
2021/0315083 A1* 10/2021 Harrison ................ H05B 45/22

FOREIGN PATENT DOCUMENTS

CN          109141627 A   *  1/2019
WO     WO-2018200685 A2   * 11/2018 .............. F21V 21/15

* cited by examiner

*Primary Examiner* — Abdullah A Riyami
*Assistant Examiner* — Syed M Kaiser
(74) *Attorney, Agent, or Firm* — MUNCY, GEISSLER, OLDS & LOWE, P.C.

(57) ABSTRACT

A system for automatically adjusting the lighting parameters of a space is disclosed herein. The control module sets the target lighting parameters in the space and drive the smart lamp groups to illuminate by using the preset light recipe and to control the smart lamp groups to perform the illumination. The control module compares an ambient light detection value in the actual environment with the target value. When the ambient light detection value is not the same as the target value, the control module drives the ambient light sensor module performs a dimming procedure to the smart lamp groups. Wherein, the dimming procedure includes the step of adjusting an illuminance uniformity of the space according to the actual illuminance detected by the ambient light sensor module. After the calculation of the illuminance uniformity formula, the illuminance uniformity is adjusted to be the same as a target illuminance uniformity.

12 Claims, 17 Drawing Sheets

(51) Int. Cl.
  *A61M 21/02* (2006.01)
  *H05B 45/12* (2020.01)
  *H05B 45/14* (2020.01)
  *H05B 45/325* (2020.01)
  *H05B 47/19* (2020.01)
(52) U.S. Cl.
  CPC ... *H05B 45/325* (2020.01); *A61M 2021/0044* (2013.01); *H05B 47/19* (2020.01)
(58) Field of Classification Search
  CPC .. A61M 2210/0606; A61M 2210/0612; A61M 2230/10; A61M 2230/62; A61M 2230/63; A61M 21/00; G16H 20/70; G16H 50/20; Y02B 20/40
  See application file for complete search history.

INTELLIGENT HUMAN CENTRIC LIGHTING SYSTEM WITH AMBIENT LIGHT MONITORING OF LIGHTING SITE ENVIRONMENT

CROSS REFERENCE TO RELATED APPLICATIONS

This application claims priority of U.S. Provisional Application No. 63/343,717 filed on May 19, 2022 under 35 U.S.C. § 119 (e), the entire contents of all of which are hereby incorporated by reference.

FIELD OF THE INVENTION

The invention relates to a system and method for establishing a multispectral lighting situational database, and in particular relates to an intelligent human centric lighting system for ambient light monitoring of the lighting site environment.

BACKGROUND OF THE INVENTION

Humans are animals with changeable emotions, they will have different emotional reactions with the individual's psychological state, such as excitement, amusement, anger, disgust, fear, happiness, sadness, serene, neutral. When negative emotions (such as anger, disgust and fear) cannot be resolved in time, they will cause psychological damage or trauma to the human body, and finally evolve into mental illness. Therefore, how to timely provide an emotional resolution or relief or treatment system that can meet the needs of users has broad business opportunities in today's society, full of high competition and high pressure at any time.

In modern medical equipment, the changes of hemodynamics caused by neuronal activity can be measured by functional Magnetic Resonance Imaging (fMRI) system. Due to the non-invasiveness of fMRI and its low radiation exposure, fMRI is currently mainly used in the study of human and animal brain or spinal cord. At the same time, the tester can also be checked by the electroencephalogram of the EEG, and the emotions can be stimulated in the same way, and the responses of different emotions can be seen, for example, the brainwave patterns of fear and happiness can be seen significantly different. Among them, when observing the response of a certain emotion under fMRI and EEG, for example, under happy emotion (which can be induced by pictures and matched with facial emotion recognition), fMRI was used to observe the blood oxygen-level dependent (BOLD) contrast response and found that in the medial prefrontal cortex (Mpfc), there were significantly more responses to the corresponding emotions (anger and fear). In contrast, for example, in the case of fear and anger, fMRI was used to observe the blood oxygen-level dependent (BOLD) contrast response, and it was found that it was significantly reflected in the amygdala region, showing that the two kinds of emotions have different response regions in the brain. Therefore, the blood oxygen-level dependent (BOLD) contrast response of different regions in the brain can be used to clearly determine which emotion the tester is currently in. In addition, if the electroencephalogram of the EEG is used to examine the measurement tester, and the emotions are stimulated in the same way, it can be seen that the brainwave patterns of fear and happiness are significantly different. Therefore, you can also determine what kind of emotion the tester is currently in through the brainwave patterns of different reactions. According to the above, for the functional Magnetic Resonance Imaging (fMRI) system, emotions are distinguished by different blood oxygen-level dependent (BOLD) contrast reactions, while for the EEG, emotions are distinguished by different brainwave patterns. It is obvious that the methods used to determine the emotion of the tester and the contents recorded are completely different. Therefore, in terms of current science and technology, the brainwave patterns of EEG cannot replace the blood oxygen-level dependent (BOLD) contrast response of functional Magnetic Resonance Imaging (fMRI) for the test results of the same emotion of the same tester.

The above discussion on emotion determination by functional Magnetic Resonance Imaging (fMRI) system and EEG is that fMRI system is very expensive and huge, so it cannot be used in commercial systems and methods of human centric lighting. Similarly, if only the brainwave patterns of the EEG are used to determine the mood of the tester, it may be encountered that the brainwave patterns of different testers for different emotions may be different. Therefore, at present, it is impossible to use the blood oxygen-level dependent (BOLD) contrast response of functional magnetic resonance imaging system (fMRI) alone, or the brain wave mode of EEG alone to construct a commercial human centric lighting method and system through the editing of light recipe. It has been demonstrated that human mood can be changed by illuminating by the process described above. Therefore, when these human centric lighting methods and systems are in the process of commercial operation, the light recipe must be accurate for the environment that provides human centric lighting and the actual light field of the lighting module in different lighting fields. In order to ensure that the lighting recipe provided by human centric lighting (for example: CCT or illuminance, etc.) can enable users to achieve the desired effect.

SUMMARY OF THE INVENTION

According to the above description, human centric lighting system for commercial use need to further detect various ambient light sources in the lighting field, especially the light that spills into the space through the windows of the building. It compensates for the influence of the target spectrum set in the lighting field so that the lighting field can maintain the lighting program in the environment of the target spectrum.

A system for automatically adjusting the lighting parameters of a space, the system includes a plurality of smart lamp groups, a plurality of ambient light sensor modules, a control module, and an interface device arranged in the space and are connected through a wireless communication protocol, and the smart lamp group and the interface device are respectively paired to the ambient light sensor module and the control module through the wireless communication protocol, the system comprising: the control module sets the target lighting parameters in the space and drive the smart lamp groups to illuminate by using the lighting parameters of the preset light recipe and to control the smart lamp groups to perform the illumination; the control module compares an ambient light detection value in the actual environment with the value of the target lighting parameters, wherein when it is determined that the ambient light detection value is the same as the value of the target lighting parameters, the ambient light sensor module continues to drive the smart lamp groups to illuminate with the lighting parameters of the preset light recipe; and when it is determined that the ambient light detection value is not the same as the value of the target lighting parameters, the control module drives the ambient light sensor module performs a dimming procedure to the smart lamp groups, wherein the dimming procedure comprising the following steps: performing the dimming procedure according to the target lighting parameters by the ambient light sensor module, so that the value of the lighting parameter in the actual environment is the same as the value of the set target lighting parameters; and adjusting an illuminance uniformity of the space according to the actual illuminance detected by the ambient light sensor module, after the calculation of the illuminance uniformity formula, the illuminance uniformity is adjusted to be the same as a target illuminance uniformity.

A method for automatically adjusting the lighting parameters of a space, wherein a plurality of smart lamp groups, a plurality of ambient light sensor modules, a control module, and an interface device are arranged in the space and are connected through a wireless communication protocol; and the smart lamp group and the interface device are respectively paired to the ambient light sensor module and the control module through the wireless communication protocol, the method comprising the following steps: driving the smart lamp groups to illuminate in the space, wherein the ambient light sensor module drives the smart lamp groups to illuminate in the space by using the lighting parameters of the preset light recipe; setting the target lighting parameters in the space by a user through the control module; driving the ambient light sensor modules to perform an ambient light detection in the space by the control module and sending the ambient light detection value to the control module; and determining if the ambient light detection value is the same as the value of the target lighting parameters, wherein the control module compares the ambient light detection value in the actual environment with the value of the target lighting parameters, wherein when it is determined that the ambient light detection value is the same as the value of the target lighting parameters, the ambient light sensor module continues to drive the smart lamp groups to illuminate with the lighting parameters of the preset light recipe; and when it is determined that the ambient light detection value is not the same as the value of the target lighting parameters, the control module drives the ambient light sensor module performs a dimming procedure to the smart lamp groups, wherein the dimming procedure comprising the following steps: performing the dimming procedure according to the target lighting parameters by the ambient light sensor module, so that the value of the lighting parameter in the actual environment is the same as the value of the set target lighting parameters; and adjusting an illuminance uniformity of the space according to the actual illuminance detected by the ambient light sensor module, after the calculation of the illuminance uniformity formula, the illuminance uniformity is adjusted to be the same as a target illuminance uniformity.

A method for automatically adjusting the lighting parameters of a space, wherein a plurality of smart lamp groups, a plurality of ambient light sensor module, a control module, and an interface device are arranged in the space and are connected through a wireless communication protocol; the smart lamp group and the interface device are respectively paired to the ambient light sensor module and the control module through the wireless communication protocol; and the control module and interface device are connected to the cloud through the Artificial Intelligence of Things, the method comprising the following steps: driving the smart lamp groups to illuminate in the space, wherein the ambient light sensor module drives the smart lamp groups to illuminate in the space by using the lighting parameters of the preset light recipe; setting the target lighting parameters in the space, wherein the control module sets the equivalent melanopic illuminance (EML) and circadian action factor (CAF) of the human circadian rhythm according to the interval of the daily time, as the target lighting parameters in the space; driving the ambient light sensor modules to perform an ambient light detection in the space by the control module and sending the ambient light detection value to the control module; and determining if the ambient light detection value is the same as the value of the target lighting parameters, wherein the control module compares the ambient light detection value in the actual environment with the value of the target lighting parameters, wherein when it is determined that the ambient light detection value is the same as the value of the target lighting parameters, the ambient light sensor module continues to drive the smart lamp groups to illuminate with the lighting parameters of the preset light recipe; and when it is determined that the ambient light detection value is not the same as the value of the target lighting parameters, the control module drives the ambient light sensor module performs a dimming procedure to the smart lamp groups, wherein the dimming procedure comprising the following steps: performing the dimming procedure according to the target lighting parameters by the ambient light sensor module, so that the value of the lighting parameter in the actual environment is the same as the value of the set target lighting parameters; and adjusting an illuminance uniformity of the space according to the actual illuminance detected by the ambient light sensor module, after the calculation of the illuminance uniformity formula, the illuminance uniformity is adjusted to be the same as a target illuminance uniformity.

According to the system and lighting method for automatically adjusting the lighting parameters of the space of the present invention, various lighting parameters in the lighting field can be controlled very precisely. For example, it at least includes illuminance (lx), Correlated Color Temperature (CCT), color rendering (Ra), equivalent melanopic illuminance (EML), circadian action factor (CAF), light flicker frequency and/or illuminance uniformity and other information. In particular, the equivalent melanopic illuminance (EML) and circadian action factor (CAF) in the lighting field must be accurate in order to determine the effect of the "light recipe" used by the user on emotional adjustment.

DETAILED DESCRIPTION OF THE PREFERRED EMBODIMENT

Figure 1A:
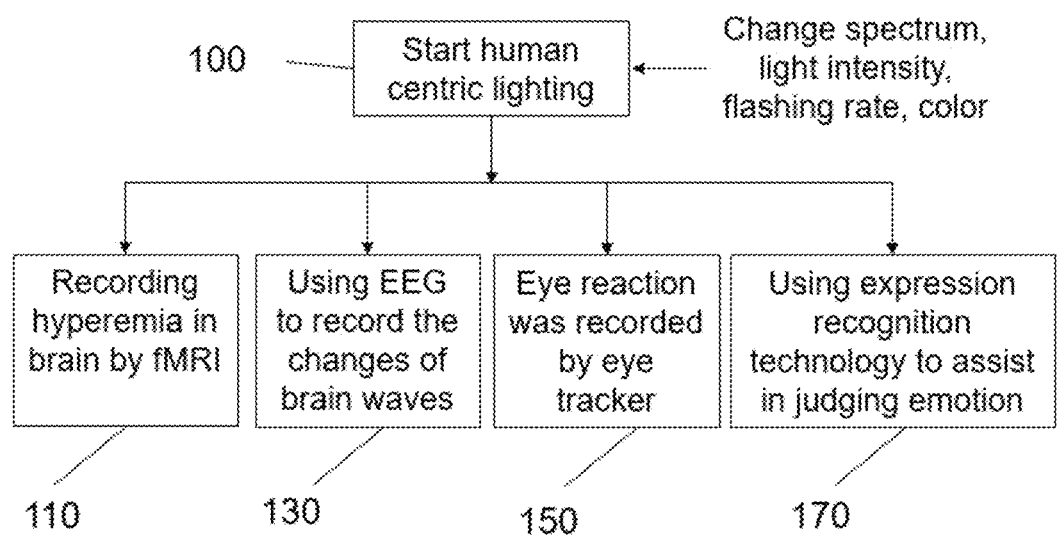
FIG. 1a is the original data collection structure of the human centric lighting to physiological and emotional according to the present invention.

In the specification after the present invention, the functional magnetic resonance imaging system is referred to as "fMRI system", the Electroencephalography is referred to as "EEG", and the blood oxygen-level dependent comparison is referred to as "BOLD". In addition, in the embodiment of the CCT test of the present invention, the test is carried out in units of every 100K. However, in order to avoid too lengthy description, in the following description, the so-called specific emotion refers to excitement or excitement, happiness, amusement, etc., and the corresponding specific emotional response will be explained with 3,000K, 4,000K and 5,700K as CCT test examples, therefore, the present invention cannot be limited to the embodiments of the three CCTs. At the same time, in order to make those in the technical field of the present invention fully understand the technical content, relevant embodiments and embodiments thereof are provided for explanation. In addition, when reading the embodiment provided by the present invention, please also refer to the schema and the following description, in which the shape and relative size of each component in the schema are only used to assist in understanding the content of the embodiment, not to limit the shape and relative size of each component.

The present invention uses fMRI system to understand the corresponding relationship between spectrum and emotion in the brain through physiological signal measurement method, and formulates a set of preliminary mechanism of using light to affect human physiological and psychological reactions, because the brain imaging of fMRI system can determine which part of the human brain has hyperemia reaction when stimulated by light, it can also record BOLD reaction. This BOLD response to brain hyperemia is also known as the "rise of blood oxygen concentration dependent response". Therefore, according to the image recording data of brain hyperemia under various emotions of fMRI system and the response of "rise of blood oxygen-level dependent response", the present invention can accurately and objectively infer the physiological and emotional changes of the tester, and then take the physiological and emotional confirmed by fMRI system as the basis, further, EEG is used to record the changes of EEG to establish the correlation between them, in order to use the changes of EEG to replace the emotion determination of fMRI system.

Therefore, the main purpose of the present invention is to enable the tester to record the BOLD response of the tester to the specific emotion after illuminating the tester during the test of specific emotion in the fMRI system, so as to screen out which specific "effective CCT" can multiply the specific emotion, the CCT of lighting is used as the "effective CCT" corresponding to specific emotions. After that, the tester is illuminated with "effective CCT", and the EEG is used to record the brainwave patterns under the stimulation of "effective CCT", so that the specific brainwave patterns of the EEG is related to the specific BOLD response. After that, the user's emotional change can be assisted by the specific EEG mode of the EEG, in order to construct a set of intelligent human centric lighting system and its method that can be operated commercially, so as to solve the problem that expensive fMRI system must be used to execute intelligent human centric lighting system, which can reduce the operation cost and further meet the customized service demand.

First, please refer to FIG. 1a, which is the original data collection framework of physiological and emotional due to human centric lighting of the present invention. As shown in FIG. 1a, starting the intelligent human centric lighting system 100 is in an environment where various adjustable lighting modules have been configured (e.g., a test space), and provides light signal lighting parameters such as spectrum, light intensity, flicker frequency and CCT that can be changed. For different target emotions, the present invention uses the fMRI compatible image interaction platform 110 formed by the fMRI system to guide the emotion of voice and image, and at the same time, it is matched with a specific effective spectrum to stimulate for 40 seconds. Observe the changes in the area where the blood oxygen-level changes in the tester's brain to verify whether the "effective CCT" can significantly induce the tester's emotional response, and the details are as follows.

Figure 1B:
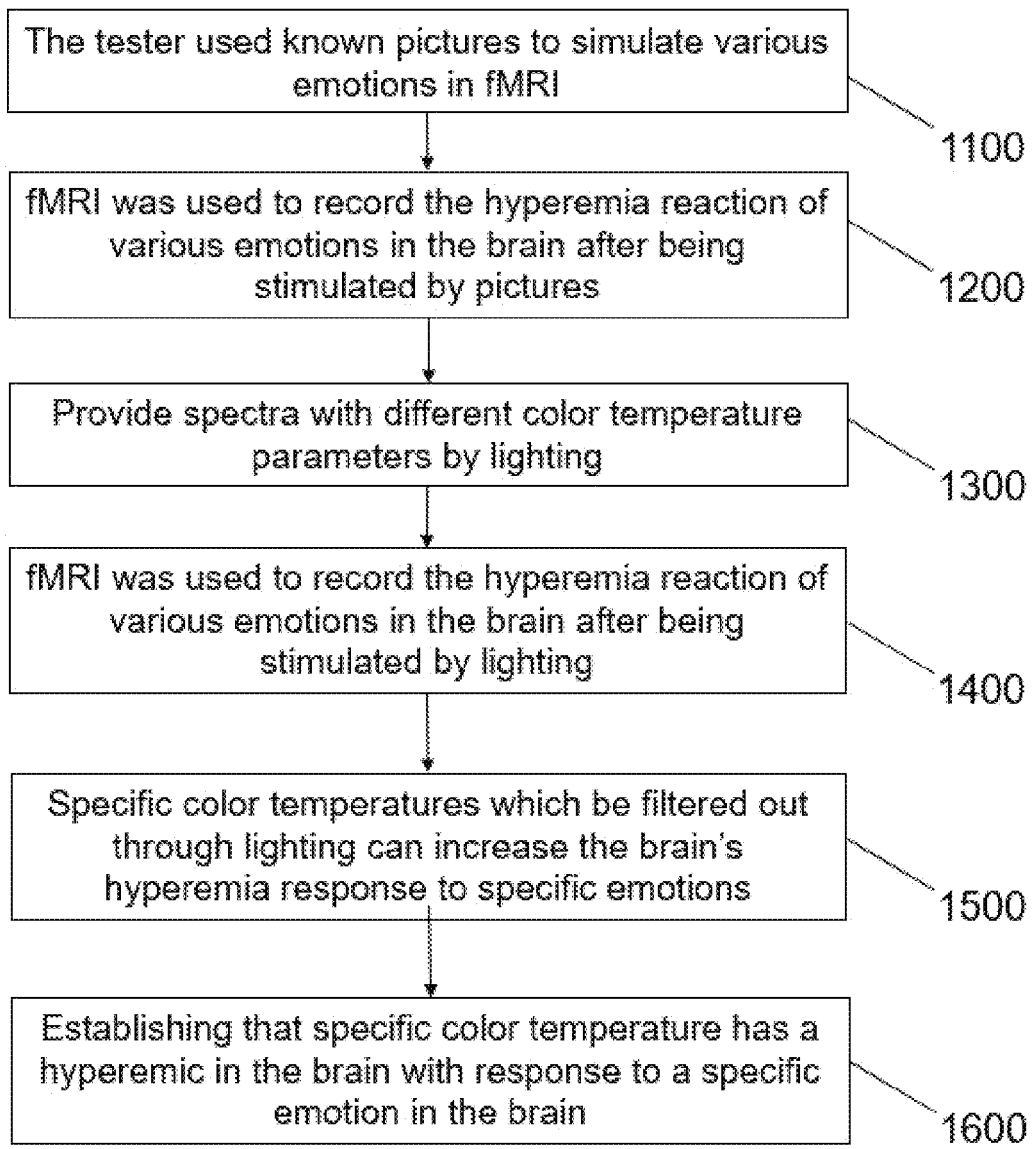
FIG. 1B is the original data collection of the human centric lighting to physiological and emotional according to the present invention.
Figure 1C:
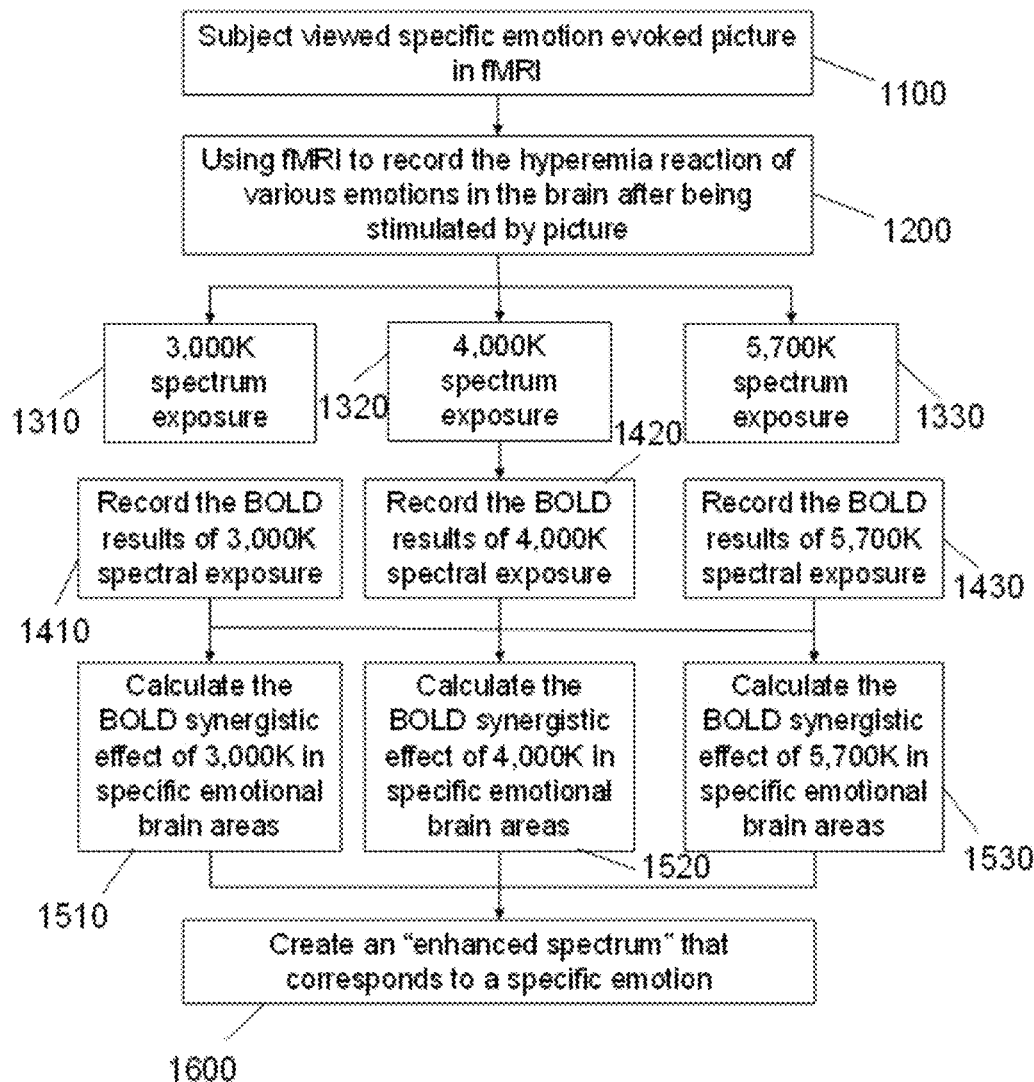
FIG. 1c is the judgment flow for the response of human centric lighting to specific physiological and emotional according to the present invention.

Next, please refer to FIG. 1b and FIG. 1c, wherein FIG. 1b is a flow chart of collecting original data of human centric lighting to physiological and emotional responses according to the present invention, and FIG. 1c is a determining flow of human centric lighting to specific physiological and emotional responses. As shown in step 1100 in FIG. 1b, each tester has been positioned on the compatible image interaction platform 110, and then each tester is guided to stimulate various emotions through known pictures. Afterwards, as shown in step 1200, the BOLD response in the brain of the tester's various emotions after being stimulated by the picture is recorded through the compatible image interaction platform 110. Next, as shown in step 1300, the tester is visually stimulated by irradiating light to provide spectrums with different CCT parameters. For example: use LED lamps with electronic dimmers to provide spectrums with different CCT parameters. In the embodiment of the present invention, nine groups of visual stimuli with different CCTs, including 2,700K, 3,000K, 3,500K, 4,000K, 4,500K, 5,000K, 5,500K, 6,000K, and 6,500K, are provided. Among them, after completing 40 seconds of effective light irradiation and stimulation each time, you can choose to give testers one minute of invalid light source lighting (full spectrum non-flicker white light) to achieve the purpose of emotional relaxation. Further, it is also possible to choose to give the tester a 40 second counter effect light stimulation to observe whether the response in the area that responded to the original effective light stimulation decreased. In the embodiment of the present invention, after the compatible image interaction platform 110 has recorded the BOLD response in the brain of the tester's specific emotion after being stimulated by the picture, the tester is visually inspected by providing spectra with different CCT parameters. The stimulus, as shown in step 1310 in FIG. 1c, is used to provide a spectrum with a CCT of 3,000K, then, as shown in step 1320, to provide a spectrum with a CCT of 4,000K, and finally, as shown in step 1330, to provide a CCT for the 5,700K spectrum, the test subjects were visually stimulated.

Next, as shown in step 1400, the BOLD response of the test subject's brain after being stimulated by light is recorded through the compatible image interaction platform 110. In the embodiment of the present invention, after the tester is stimulated by lighting with different CCT parameters, the compatible image interaction platform 110 records the BOLD response results with emotional response areas in the corresponding limbic system of the tester in sequence. Among them, the location of limbic system triggered by different emotions is different, and the above limbic system with emotional response in brain area is shown in Table 1 below.

TABLE 1

| Limbic system | Function |
|---|---|
| ACC | Emotion |
| Cuneus | Vision, Control bipolar disorder |
| Cerebellum | Balance, Coordination, Antidepressant & Anxiety |
| Insula Lobe | Affection, addiction |
| Lingual Gyrus | Logic, Vision, Antidepressant & Anxiety |
| Rolandic Operculum | Emotion Management, Gustatory Sense |
| Superior Frontal Gyrus | Working Memory, Self-consciousness, laugh |
| Middle Temporal Gyrus | Emotion Recognition, Creativity |
| MCC | Emotion |
| Pallidum | Affection, Motion, Cognition, Reward System |
| Temporal Pole | Affection, Language, Auditory |

The compatible image interaction platform 110 records the response result of BOLD in a specific area of the brain, and the response result is determined by calculating the area of these emotional response parts when the brain area has more limbic system with BOLD emotional response, for example: when there is a BOLD emotional response The larger the area of emotional response, the stronger the response to a specific physiological and emotional. In the embodiment of the present invention, as shown in step 1410 in FIG. 1c, it is used to record the reaction result of BOLD with a CCT of 3,000K after spectral irradiation, and then, as shown in step 1420, it is used to record the CCT of 4,000K. Finally, as shown in step 1430, the reaction result of BOLD after spectral irradiation is used to record the reaction result of BOLD after spectral irradiation with a CCT of 5,700K. Among them, after the tester passes through the lighting procedure after the excitement is induced, the compatible image interaction platform 110 records the response results of BOLD in a specific area of the brain as shown in Table 2. Obviously, when the CCT of 3000K is irradiated, the excitement can be enhanced. Therefore, according to the results of the embodiments of the present invention, the optimal stimulating CCT is between 3000K and 4000K. However, it should be noted that after exposure to a CCT of 5700K, there will be a negative inhibitory effect on the excitement.

TABLE 2

Excitement Index

| Limbic system | 3,000K | 4,000K | 5,700K |
|---|---|---|---|
| ACC | 0 | 0 | −30 |
| Cerebellum | 577 | 0 | −75 |
| Middle Temporal Gyrus | 0 | 99 | 0 |
| Superior Frontal Gyrus | 0 | 127 | 0 |
| Total T Score | 577 | 226 | −105 |

Among them, after the tester passes through the lighting procedure induced by happiness, the compatible image interaction platform 110 records the response results of BOLD in a specific area of the brain as shown in Table 3. Obviously, when the CCT of 4000K is irradiated compared with the other CCTs, the CCT of 4000K can enhance the BOLD response of the brain area in the happiness. Therefore, according to the results of the embodiments of the present invention, the optimal stimulating CCT of happiness is around 4000K.

TABLE 3

Happiness Index

| Limbic system | 3,000K | 4,000K | 5,700K |
|---|---|---|---|
| ACC | 0 | 0 | −162 |
| Cerebellum | 163 | 252 | 0 |
| Pallidum | 80 | 0 | 0 |
| Insula Lobe | 85 | 307 | 0 |
| Lingual Gyrus | 0 | 58 | 403 |
| Temporal Pole | 0 | 57 | 0 |
| Total T Score | 328 | 674 | 241 |

Among them, after the tester passes through the lighting procedure after the emotion-induced amusement, the compatible image interaction platform 110 records the response results of BOLD in a specific area of the brain as shown in Table 4. Obviously, all CCTs can enhance the BOLD response of the brain area of amusement, especially when the CCT is higher, the BOLD response of the brain area of amusement is stronger.

TABLE 4

Amusement Index

| Limbic system of brain | 3,000K | 4,000K | 5,700K |
|---|---|---|---|
| Lingual Gyrus | 0 | 279 | 327 |
| Cerebellum | 539 | 215 | 226 |
| Middle Temporal Gyrus | 0 | 0 | 90 |
| MCC | −83 | 32 | 0 |
| Total T Score | 456 | 526 | 643 |

Among them, after the tester passed the lighting program induced by the emotion of the serene index, the compatible image interaction platform 110 recorded the response results of BOLD in specific areas of the brain, as shown in Table 5. Obviously, when the low CCT of 3000K is irradiated, it can enhance the sense of tranquility or relaxation. However, when the CCT is higher, it will have a negative inhibitory effect on the mood of the serene. In particular, the higher the CCT, the more negative the suppression effect will be.

TABLE 5

Serene Index

| Limbic system of brain | 3,000K | 4,000K | 5,700K |
|---|---|---|---|
| ACC | 0 | 32 | 0 |
| Cerebellum | 151 | 0 | 221 |
| Cuneus | 0 | 0 | −789 |
| Lingual Gyrus | 298 | 0 | 107 |
| Middle Temporal Gyrus | 0 | −134 | 0 |
| Superior Frontal Gyrus | 0 | 0 | −598 |
| Total T Score | 449 | −102 | −1059 |

Afterwards, as shown in step 1500, the results of the BOLD reaction that a specific CCT can increase a specific emotion are screened by lighting, and the specific CCT is called an "effective CCT". In this embodiment, the BOLD response result of the emotional response area in the limbic system of the tester's corresponding brain is recorded, so as to summarize the stimulation effect of CCT on the brain, as shown in Tables 2 to 5 shown. For the BOLD brain region-dependent response results that screened out the specific CCT that can increase a specific emotion, we calculated those specific CCT that can make the response effect of a specific emotion reach the maximum response value (that is, the maximum response area value with BOLD).

As shown in step 1510, when the tester has recorded the excitation emotion on the compatible image interaction platform 110 and finishes the lighting program again, the maximum response value is calculated. For example, according to the records in Table 2, the total score of 3,000K (577) is subtracted from the total score of 4,000K (226) to obtain 351. Then, after subtracting the total score (−105) of 5,700K from the total score (577) of 3,000K, 682 is obtained. Therefore, the total score of the response value after the excitement is induced under the illumination of 3000K is 1033.

Next, as shown in step 1520 in FIG. 1c, when the tester has recorded the excitation emotion on the compatible image interaction platform 110 and completed the lighting program again, it starts to calculate the maximum response value. For example, according to the records in Table 2, subtract the total score (226) of 4,000K from the total score (577) of 3,000K to obtain −351. Then, after subtracting the total score (−105) of 5700K from the total score (266) of 4,000K, 371 is obtained. Therefore, the total score of the response value after the excitement is induced under the illumination of 4000K is 20.

Then, as shown in step 1530 in FIG. 1c, after the tester has recorded the excitation emotion induction on the compatible image interaction platform 110 and completed the lighting program, it starts to calculate the maximum response value. For example, according to the records in Table 2, after subtracting the total score (−105) of 5,700K from the total score (577) of 3,000K, it obtains −682. Then, the total score (−105) of 5,700K is subtracted from the total score (266) of 4,000K to obtain −371. Therefore, the total score of the response value after the excitement emotion is induced under the illumination of 5700K is −1033.

According to the above calculation, after the excitation emotion is induced, the excitation emotion can reach the maximum response value at 3,000K lighting. That is, 3,000K illuminance can make excitement get a more obvious additive effect (that is, compared with the total calculated score of 4,000K and 5,700K illuminance, the total calculated score of 3,000K illuminance is 1033, the highest). Therefore, 3,000K illuminance is used as the "effective CCT" of excitement. For other emotions, such as "effective CCT" of happiness, amusement and serene, different "effective CCTs" can be obtained from the above calculation results in steps 1510 to 1530, as shown in Table 6 below.

TABLE 6

| Emotion | Effective CCT |
|---|---|
| Excitement | 3,000K |
| Happiness | 4,000K |
| Amusement | 5,700K |
| Serene | 3,000K |

Next, according to the statistical results in Table 6, the effective CCT can be regarded as the result of a specific physiological and emotional-dependent response, and this effective CCT can be regarded as the "enhanced spectrum" of the "blood oxygen-level dependence" of fMRI on a certain emotion. Wherein, the optimal stimulating CCT should fall between 3000K and 4000K. For example, an effective CCT of 3,000K can represent the "enhanced spectrum" of the fMRI system in "excited" emotions. For example, an effective CCT of 4,000K can represent the "enhanced spectrum" of the fMRI system in "happy" emotions. Wherein, the optimal stimulating CCT of happiness should fall around 4000K. For example, the effective CCT of 5,700K can represent the "enhanced spectrum" of the fMRI system in "amusement" emotions. For example, an effective CCT of 3,000K can represent the "enhanced spectrum" of the fMRI system in "serene" emotions. Wherein, the optimal stimulating CCT of serene should fall around 3000K.

Finally, as shown in step 1600, the light recipe database of the enhanced spectrum corresponding to the effect of a particular emotion can be established in the fMRI system. The tester is stimulated by the above-mentioned human centric lighting parameters, and the BOLD response of the tester's brain when the tester's brain is stimulated by light is observed and recorded through the fMRI system. The additive and multiplicative response of "blood oxygen-level dependence increase" makes a specific effective CCT can be regarded as the "enhanced spectrum" of the "light recipe database" of fMRI for a specific emotion. Obviously, the present invention objectively deduces the tester's "light recipe" under a specific physiological and emotional response based on the statistical result of the BOLD reaching a specific emotional response at a specific "effective CCT" in Table 6, and This "light recipe" is used as the evidence of the most synergistic physiological and emotional response to a specific emotion. (Including: excitement, happiness, amusement, anger, disgust, fear, sadness, calm, or neutrality)

It should be emphasized that, in the entire implementation process of FIG. 1b and FIG. 1c, the statistical results in Table 5 are obtained after 100 testers are respectively subjected to a complete test of multiple specific emotions. For example, in terms of excitement, providing an effective CCT of 3,000K as the "enhanced spectrum" under the excited physiological as the light recipe and emotional response can make the tester's excited emotions produce the most synergistic physiological-emotional response. For example, in terms of happy emotions, providing an effective CCT of 4,000K as the "enhanced spectrum" under the happy physiological as the light recipe and emotional response can make the tester's happy emotions produce physiological and emotional responses with the strongest synergistic effect. Another example: in terms of amusement emotions, providing an effective CCT of 5,700K as an "enhanced spectrum" under the amusement physiological as the light recipe and emotional response can make the tester's amusement emotions produce a physiological and emotional response with the strongest synergistic effect.

In addition, it should also be emphasized that the above-mentioned three CCTs are only representative of the embodiments of the present invention, and not only the lighting of the three CCTs are used as the "enhanced spectrum" under the three physiological and emotional responses. In fact, the whole process of FIG. 1b and FIG. 1c can be carried out for different emotions (including excitement, happiness, amusement, anger, disgust, fear, sadness, calm or neutral) after 2,000K CCT is increased by 100K as an interval. Therefore, Table 5 of the present invention is only the result of the disclosure part, not to limit the present invention. The invention is only limited to these embodiments.

Next, the present invention is to establish an artificial intelligence model of "the correlation between brainwaves and brain images of general physiological and emotional", so that in future commercial promotion, the results of other sensing devices can be directly used to infer physiological and emotional without using fMRI system. Among them, the sensing device matched with the present invention includes electroencephalography (EEG). In the following embodiments, the electroencephalography (EEG) 130 is used to establish the human centric physiological and emotional response to light, and the eye tracker 150 or the expression recognition technology auxiliary program 170 can be used to replace the fMRI system's response to physiological and emotional. However, the eye tracker 150 or the expression recognition technology auxiliary program 170 will not be disclosed in the present invention, but will be announced first.

Figure 2A:
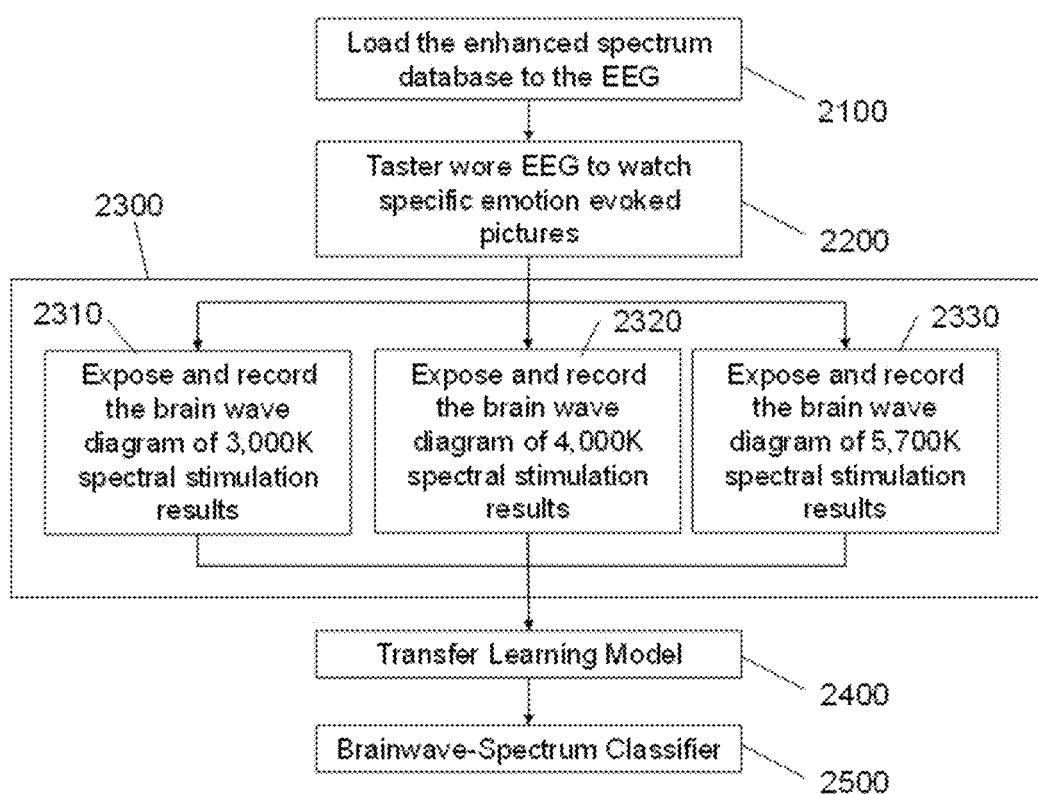
FIG. 2a is a method for establishing the response of EEG of human centric lighting to physiological and emotional.

Please refer to FIG. 2a, which is a method for establishing a human centric lighting electroencephalogram response to physiological and emotional according to the present invention. As shown in FIG. 2a, the present invention is a method for establishing the human centric lighting response to physiological and emotional through the EEG 130, including: first, as shown in step 2100, the "enhanced spectrum" database information in Table 5 is also stored in the memory of the EEG 130. Next, as shown in step 2200, let the testers wear the EEG, and guide each tester to stimulate various emotions through the elements of known pictures or videos. For example, the emotional stimuli of known pictures or videos can be selected from the International Affection Picture System (IAPS). Afterwards, as shown in step 2300, the intelligent human centric lighting system 100 is activated, and light signal parameters such as spectrum, light intensity, flicker frequency, and CCT that can be changed are provided to stimulate the tester with light. Next, the electroencephalogram file after being illuminated with different CCTs under a specific emotion is recorded by the EEG 130. For example, in this embodiment, each tester is first stimulated with excitement, and then, in steps 2310 to 2330, different CCTs of 3,000K, 4,000K and 5,700K are provided to stimulate the tester respectively, and the tester is recorded in when stimulated by excitement, the electroencephalogram file of the specific emotion after the tester is illuminated with different CCTs is stored in the device in the memory of the EEG 130. In the embodiment of the present invention, the electroencephalogram files after 100 testers have completed specific emotional stimulation and lighting have been recorded respectively, therefore, a larger memory is required.

Next, as shown in step 2400, the electroencephalogram files of specific emotions (e.g., excitement, happiness, amusement) stored in the memory of the EEG 130 is learned through the learning method of artificial intelligence. Since the EEG 130 can only store the waveform of the electroencephalogram, the electroencephalogram currently stored in the memory of the EEG 130 is the electroencephalogram file after a known specific triggering emotional stimulus and lighting of different CCTs. It should be noted that, in the actual test, different testers have different electroencephalogram files for the same emotional stimulus and lighting with the same CCT. Therefore, during the learning process of step 2400, the present invention needs to classify the electroencephalogram files of specific emotions through the information of the light recipe database the "enhanced spectrum". Group the electroencephalogram files with a CCT of 3,000K, for example: For the electroencephalogram files of happy emotions, only group the electroencephalogram files of different testers with a CCT of 4,000K. Another example: for the electroencephalogram file of happy mood, only the electroencephalogram files of different testers at 4,000K CCT are grouped; for example, for the electroencephalogram file of happy mood, only the electroencephalogram files of different testers at 5,700K CCT are grouped. Then, the EEG is trained through machine learning in artificial intelligence. In the embodiment of the present invention, in particular, a transfer learning model is selected for learning and training.

In the process of learning and training using the transfer learning model in step 2400, the group of electroencephalogram files for specific emotions is learned and trained by counting, calculating and comparing the similarity. For example, when learning and training the group of electroencephalogram files with 3,000K CCT, it is based on statistics, calculation and comparison of the ranking of the highest similarity and the lowest similarity among the electroencephalogram files with 3,000K CCT. For example: the ranking with the highest similarity can be regarded as the electroencephalogram file with the strongest emotion, the ranking with the lowest similarity can be regarded as the electroencephalogram file with the weakest emotion, and the electroencephalogram file with the strongest emotion can be regarded as the electroencephalogram file. As the "target value", the electroencephalogram file with the weakest emotion ranking is used as the "starting value". For the convenience of explanation, the most similar at least one electroencephalogram file is taken as the "target value", and the least similar at least one electroencephalogram file is taken as the "start value", and different scores are given, for example: "target value" is given 90 points for similarity, and 30 points for "initial value". Similarly, complete the electroencephalogram files of the series of happy emotions in the 4,000K CCT category, and the electroencephalogram files of the series of the surprised emotions in the 5,700K CCT category. Among them, the "start value" and "target value" can be formed into a score interval of similarity.

Afterwards, as shown in step 2500, an electroencephalogram classification and grading database in artificial intelligence (it may be referred to as an artificial intelligence electroencephalogram file database) is established. After the step 2400 is passed, the classification results of the "target value" score and the "start value" score are given to the electroencephalogram file groups of various specific CCTs to form a database, which is stored in the memory of the EEG 130. The purpose of establishing the electroencephalogram classification and grading database in step 2500 of the present invention is to obtain the electroencephalogram file of the unknown tester after receiving a specific emotional stimulus and giving lighting of a specific CCT to an unknown tester. After the similarity score interval between the electroencephalogram file of the unknown tester and the electroencephalogram file in the database is compared, it can be used to determine or infer the current state of the unknown tester's hyperemia reaction in the brain. The detailed process is shown in FIG. 2b shown.

Figure 2B:
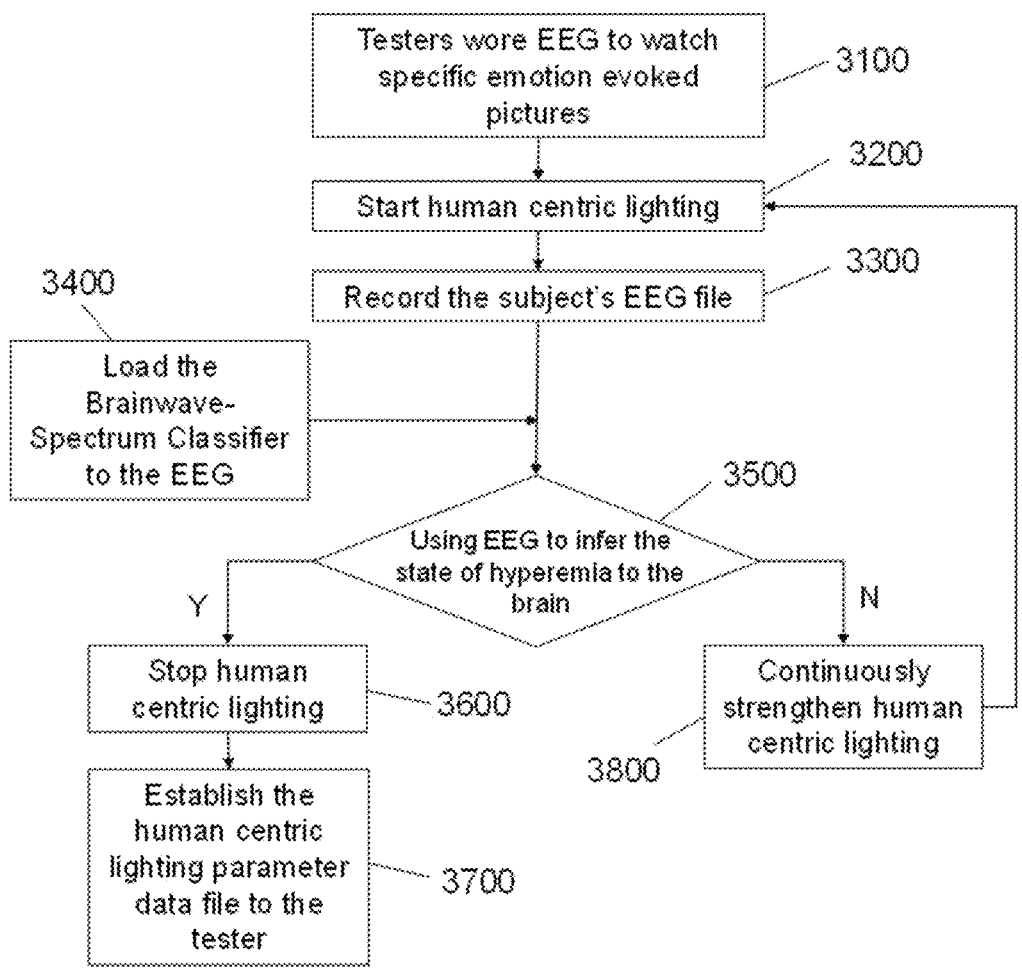
FIG. 2b is the lighting database that the present invention constructs the user to carry out effective human centric lighting.
Figure 3:
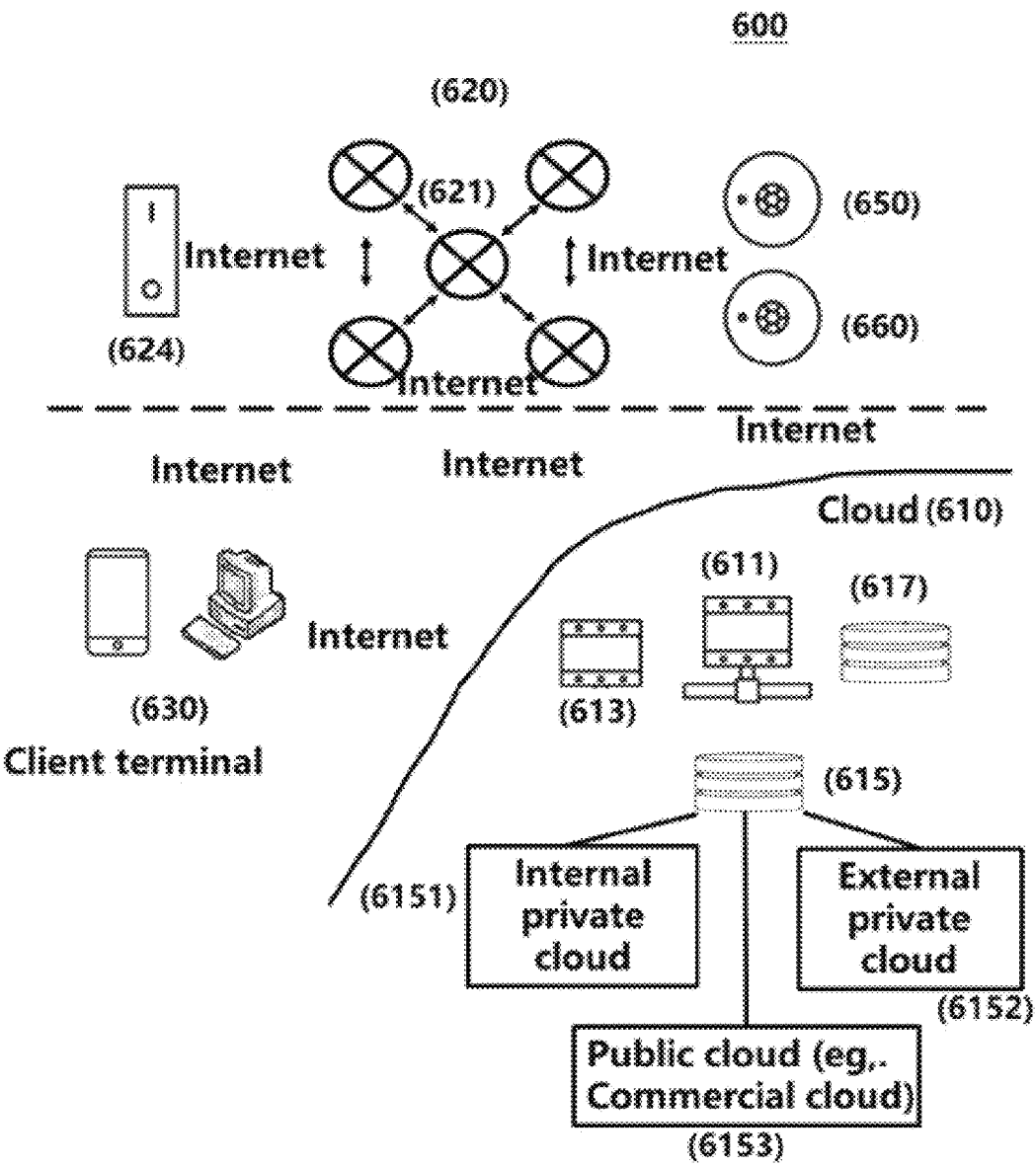
FIG. 3 is the system frame diagram of the intelligent human centric lighting system of the present invention.

Next, please refer to FIG. 2b, which is a lighting database for constructing a user's effective human centric lighting according to the present invention. First, as shown in step 3100, the tester is put on the EEG 130, and the tester is allowed to watch a picture evoked by a specific emotion. Afterwards, as shown in step 3200, the intelligent human centric lighting system 100 is activated to irradiate the tester with the light recipe by management control module 611 (as shown in FIG. 3) in an environment (e.g., a test space) that has been configured with various adjustable multispectral lighting modules. To provide lighting parameters such as spectrum, light intensity, flashing rate, CCT, exposure time and other light signal light parameters that can be changed. Next, as shown in step 3300, obtain and record the electroencephalogram file of the tester after the induced emotion and lighting, and store it in the memory module 617 of the cloud 610 (as shown in FIG. 3). Next, as shown in step 3400, import the artificial intelligence electroencephalogram file database into the management control module 611. Wherein, the management control module 611 will set a score of whether the similarity is sufficient. For example, when the similarity score is set to be more than 75 points, it means that the tester's brain hyperemia reaction is sufficient. Next, as shown in step 3500, in the management control module 611, the similarity between the tester's electroencephalogram file and the artificial intelligence electroencephalogram file is compared. For example: when the similarity score of the tester's electroencephalogram files after comparison is 90 points, the management control module 611 immediately determines that the tester's brain hyperemia reaction is very sufficient, so it will go to step 3600 to terminate the person with a specific emotion Due to lighting test. Next, go to step 3700, record the human centric lighting parameters in the tester's brain when the hyperemia response has reached the stimulus, into a database and store in the memory module 617.

Next, in the procedure of step 3500 in FIG. 2b, if the similarity score after the comparison between the tester's electroencephalogram file and the artificial intelligence electroencephalogram file is 35 points, the management control module 611 will determine the tester's brain If the hyperemia reaction is insufficient, step 3800 will be performed, and the management control module 611 will continue to strengthen the human centric lighting test, including: according to the similarity score, the management control module 611 can control it to provide an appropriate increase in the lighting time or increase light intensity. Then, the electroencephalogram file after increasing the lighting time or intensity is obtained again through step 3300. After step 3400, the human centric lighting test is not stopped until the similarity score reaches the set similarity score of more than 75 points. Wherein, when the management control module 611 determines that the hyperemia reaction in the tester's brain has reached the stimulation, in step 3700, a data file of the human centric lighting parameters of the tester is created. Finally, the management control module 611 will form a "human centric lighting parameter database" of the human centric lighting parameters of each tester and store it in the memory module 617. Obviously, when there are more testers, the artificial intelligence electroencephalogram file database of the present invention will learn more electroencephalogram files, so that the similarity score of the present invention is more and more accurate.

After the artificial intelligence model of the "human centric lighting parameter database" is established, after the intelligent human centric lighting system 100 is activated, the present invention can deduce the result only by observing the electroencephalogram file of the EEG 130, that is, it can be deduced The physiological and emotional changes in the brain images of the new test subjects can be inferred based on the artificial intelligence model of the "Human Centric Lighting Parameter Database" without using a high-value fMRI system. So that the intelligent human centric lighting system 100 can be promoted and used commercially. In addition, in order to enable the "human centric lighting parameter database" to be used commercially, the "human centric lighting parameter database" may be further stored in the internal private cloud 6151 in the cloud 610.

Next, please refer to FIG. 3, which is a system architecture diagram of the intelligent human centric lighting system 100 of the present invention. As shown in FIG. 3, the overall architecture of the intelligent human centric lighting system 100 of the present invention can be divided into three blocks, including: a cloud 610, a lighting field end 620 and a client terminal 630. The internet is used as a connection channel, so the three blocks can be distributed in different areas, and of course they can be configured together. The cloud 610 further includes: a management control module 611, which is used for cloud computing, cloud environment construction, cloud management or use of cloud computing resources, etc., and also allows users to access, construct or modify the content in each module through the management control module 611. The consumption module 613 is connected with the management control module 611 and is used as a cloud service subscribed and consumed by the user. Therefore, the consumption module 613 can access various modules in the cloud 610. The cloud environment module 615, connected with the management control module 611 and the consumption module 613, divides the cloud background environment into an internal private cloud 6151, an external private cloud 6153, and a public cloud 6155 (for example, a commercial cloud), etc., and can provide system providers or an interface to a user's external or internal service. The memory module 617 is connected to the management control module 611 and is used as a storage area of the cloud background. The technical contents required to be executed by each module in the present invention will be described in detail in the subsequent different embodiments. The lighting field end 620 can communicate with the cloud 610 or the client terminal 630 through the internet. The lighting field end 620 is provided with a LED lamp group 621 composed of a plurality of light-emitting devices. And the client terminal 630 can communicate with the cloud 610 or the lighting field end 620 through the internet. Among them, the client terminal 630 of the present invention includes general users and editors who use the intelligent human centric lighting system 100 of the present invention for various commercial operations, all of which belong to the client terminal 630 of the present invention, and the representative device of the client terminal 630 or the device can be a fixed device with computing function (including with edge operations) or a portable intelligent communication device. In the following description, the user, creator, editor or portable communication device can all represent the client terminal 630. In addition, in the present invention, the above-mentioned internet may be an Artificial Intelligence of Things (AIoT).

Figure 4:
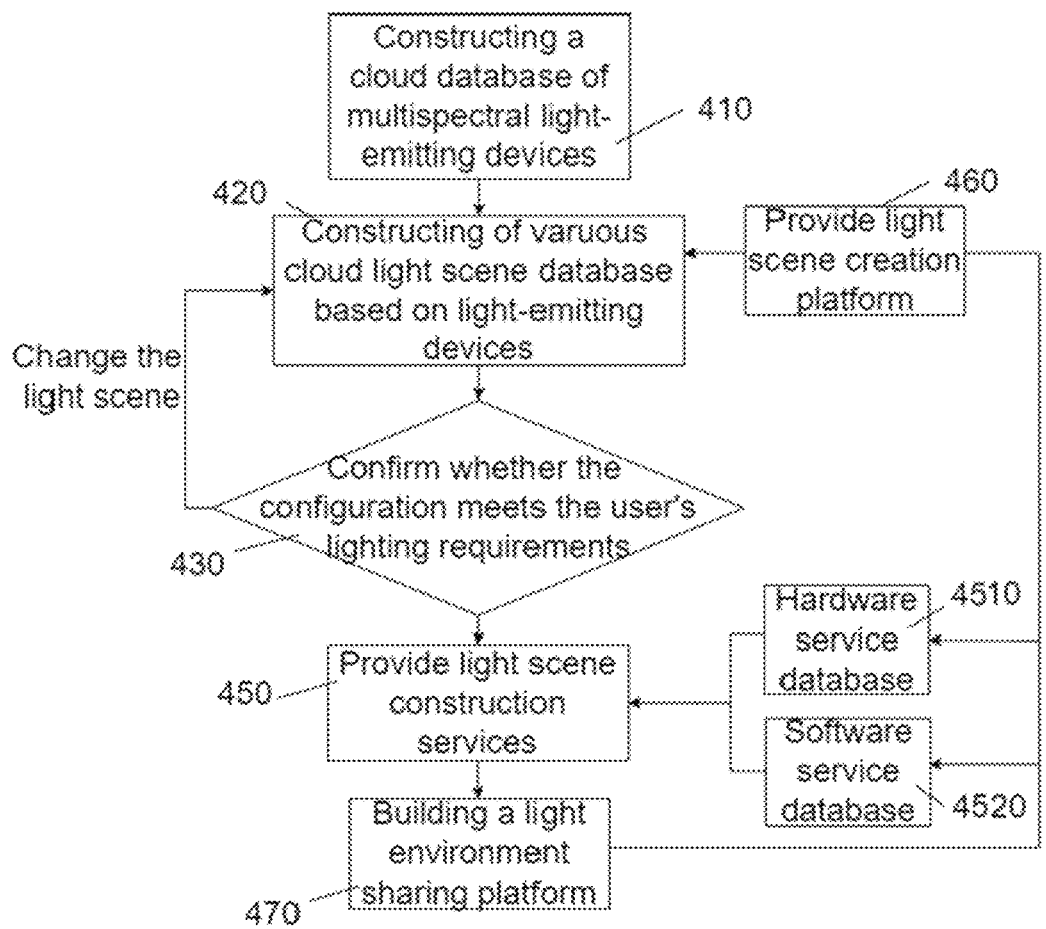
FIG. 4 is a method for constructing a human centric light environment platform of the present invention.

Please refer to FIG. 4, which is a method for constructing light environment sharing platform 400 according to the present invention. In the process of FIG. 4, the process is performed in the system of the intelligent human centric lighting system 100 in FIG. 3, wherein the intelligent human centric lighting system 100 has a plurality of LED lamp group 621 providing different spectrums. In particular, the present invention should illustrate that the LED lamp group can selectively modulate the voltage or current of the individual LED lighting to combine a light recipe with a specific CCT, so as to provide a light recipe for lighting. Of course, the present invention can also choose to use a plurality of LED lamps with a specific luminous spectrum, by providing a fixed voltage or current to make each LED lamps that is energized emit its specific spectrum to combine a light recipe with a specific CCT come to light. In addition, it should be emphasized that the LED lamp group 621 with different spectrums in the present invention need to emit different spectrums through a plurality of LED lamp groups 621 in the actual lighting process. Therefore, the different spectrums can be composed of different LED lamp group 621 with same spectrum or different spectrums. The spectrum of light-emitting devices can also be composed of multiple identical light-emitting devices, and the spectrum emitted by the light-emitting devices can be modulated into different spectrums by controlling the power provided by the device. Therefore, the present invention does not limit the embodiments of the above LED lamp group 621 with different spectrums, and of course also includes light-emitting devices with different spectrums formed by other means.

First, as shown in step 410, a multispectral light emitting device cloud database is constructed. The "human centric lighting parameter database" stored in the memory module 617 or stored in the internal private cloud 6151 is loaded into the management control module 611 by the management control module 611 in the cloud 610. Among them, the "human centric lighting parameter database" stored in the cloud 610 already knows that various CCTs can make people (or users) get corresponding emotional stimulation. for example, in Table 6, a specific CCT can make a specific emotion have a stimulating effect of a multiplicative response.

Next, as shown in step 420, a cloud database of light scenes of the multispectral lighting device is to be constructed. Since each CCT can be combined by different light recipes, that is to say, the same CCT can be combined by different light recipes. For example, when we want to build a spectrum that can provide 4,000K CCT, we can choose the light recipe of Maldives at 4,000K CCT, or we can choose the light recipe of 4,000K CCT in Bali, Indonesia, or further choose Monaco Beach at 4,000K light recipe of CCT. Obviously, these light recipes with a CCT of 4,000K have different light recipes according to their geographical location (including latitude and longitude), time/brightness/flashing rate and other factors. Therefore, in step 420, according to the relationship between the CCT and the corresponding emotions in the "human centric lighting parameter database", the cloud 610 can collect different light recipes of all kind of specific CCTs in different geographical locations on the earth, for example, collecting on the earth different light recipes at 4,000K CCT in different geographic locations (e.g., 4,000K CCT at different latitude and longitude), or collect different light recipes at 4,000K CCT at different times on earth (e.g., 4,000K CCT at 9:00 am). Afterwards, the collected different light recipes of different geographic locations on the earth at specific CCTs are also stored in the memory module 617. Through the control of the management control module 611 in the intelligent human centric lighting system 100, the parameters of various light recipes with specific CCT (i.e., time at different geographical locations or locations) can be adjusted by controlling a plurality of LED lamp group 621 with different spectra, which are stored in the memory module 617. The intelligent human centric lighting system 100 of the present invention can construct a "cloud database of multispectral light-emitting devices" with various CCTs formed in different geographical locations. Obviously, the "multispectral light emitting device cloud database" constructed in step 420 is the preset light recipe obtained from the adjustment by multiple LED lamp group 621 with different spectra. For example, each multispectral obtains is a light recipe adjusted by the light lamp group 621 by adjusting or controlling color rendering (Ra), strobe, illuminance, and CCT. In addition, it should be emphasized that after mastering the stimulation effect that different specific CCTs can make specific emotions have additive reaction, when forming the light recipe of various CCTs, in addition to the light recipe according to different geographical locations on the earth, the present invention can also consider different longitude and latitude/time/brightness/flicker frequency and other factors through artificial intelligence, The invention does not limit the synthesis or combination of light recipes different from the actual geographical location. Obviously, in step 420, the present invention has constructed a preset light recipe database. Therefore, according to the constructed database, the intelligent human centric lighting system 600 can provide lighting services with the preset light recipe through the lamp group 621. At this time, the "light recipe cloud database" constructed in step 420 can be stored in the memory module 617 or in the internal private cloud 6151 or in the public cloud 6155 (e.g., commercial cloud).

As shown in step 430, it is determined whether the lighting of the light recipe is effective. Since different users may have different effects on emotional stimulation or influence through the spectrum of human centric lighting, it is necessary to adjust the lighting spectrum of the light recipe. When the client terminal 630 enters the intelligent human centric lighting system 100 of the present invention, he can go through the management control module 611 to the memory module 617 or the "multispectral lighting device cloud database" in the internal private cloud 6151 or the public cloud 6155, select the preset light recipe with the emotion you want to achieve. After that, the management control module 611 can go to the memory module 617 or the "multispectral lighting device cloud database" in the internal private cloud 6151 or the public cloud 6155, select a default light recipe, and control LED lamp group 621 to adjust the light recipe of the desired mood, and let the adjusted light recipe perform a lighting program for the user. For example, when the user wants to adjust the mood to happiness or amusement, according to the "human centric lighting parameter database", the user can choose to use the light recipe with the CCT of 4,000K to illuminate. At this time, the user can go to the default light recipe provided by the "multispectral lighting device cloud database", or the user can choose a light recipe that can provide the CCT of 4,000K, of course, the user can also choose a specific light recipe used by the most people for irradiation.

Next, as shown in step 430, when the user selects a light recipe preset as happiness or amusement (for example, the system defaults to the light recipe of Maldives at 4,000K CCT), and carries out the lighting program through the light recipe adjusted by a plurality of LED lamp group 621 with different spectra, for example, after 15 minutes of lighting program, The user can judge or evaluate whether the light recipe of irradiation has effectively achieved happiness or pleasant emotion. Among them, the way for users to judge or evaluate whether they have effectively achieved happiness or amusement emotions can be determined according to their own feelings.

Continuing as shown in step 430, when the user intuitively feels that he or she has effectively achieved a happy or amusement mood, the user experience can be recorded and stored in the external private cloud 6153 or the public cloud 6155, for example, after the record of use experience is stored in the external private cloud 6153, it can be used as the user's own use experience file. For example, of course, the use experience can also be recorded and stored in the public cloud 6155 to provide reference for other users. If the user does not feel happy or amusement after 15 minutes of lighting, the user can adjust the light recipe through the management control module 611, for example, adjust the lighting time to 30 minutes, or replace for a light recipe, for example, go back to step 420 to reselect another light recipe, and replace the light recipe from the default Maldives to Bali, Indonesia. After that, in step 430, the multispectral lighting procedure is performed again for 15 minutes, and after the lighting procedure is completed, it is judged or evaluated again whether the lighting of Bali's light recipe has effectively achieved a happy or amusement. Until the user feels that after the multispectral lighting of the current light scene, the happy or amusement mood has been effectively achieved, the effective light scene use experience can be recorded and stored to form a "spectral recipe", and finally, and store this "spectral recipe" in the external private cloud 6153 or the public cloud 6155 to form a sharing platform. Obviously, there are multiple "spectral recipe" stored in the sharing platform. The contents stored in the sharing platform include: the lighting control parameters of the light recipe in which the user achieves the specific emotional effect.

Finally, as shown in step 470, a light environment sharing platform is constructed. After the user records and stores the effective use experience in the external private cloud 6153 or public cloud 6155, in addition to being the user's own use experience file, the intelligent human centric lighting system 100 can record and store the effective experience data of many users in the internal private cloud 6151 or public cloud 6155 after massive data analysis in step 470, The information stored in the public cloud 6155 forms a "sharing platform" of the optical environment. For example, the intelligent human centric lighting system 100 can analyze the massive data of many users' experience data, and then can obtain the ranking of the "spectral recipe" of different light scenes with specific CCT selected by the user. This ranking can provide a reference for the user to select the "spectral recipe". Further, after analyzing these massive data, we can get different indicators to provide users with reference. For example, in terms of different light recipes of 4,000K CCT, different usage orders can be made according to the user's gender, age, race, season, time, etc., so that the light environment sharing platform constructed by the present invention can be used as other designers who are interested or willing to provide human centric light recipe, use these indicators for commercial services and operations. Therefore, the light environment platform constructed by the present invention can allow the intelligent human centric lighting system 100 to provide various usage experiences after curation or algorithm operation as the default light recipe. In addition, users can also choose a "spectral recipe" that is most selected by the user for lighting according to the user experience data after calculation.

In the embodiment of FIG. 4, step 450 can exist selectively. For example, if the user only establishes the database for user's own use, user can directly store the use experience in the light recipe sharing platform after determining that it is valid in step 430 without this step 450. For example, it records and stores the effective use experience in the external private cloud 6153 or public cloud 6155. The database of the "spectral recipe" construction service to be constructed in step 450 will be described in the following embodiments.

Next, in FIG. 4, there is another embodiment that can be used for commercial services and operations, it can provide an authoring platform that allows different users or creators to create new "spectral recipe" through this authoring platform. As shown in step 460, a "spectral recipe" authoring platform is provided in the intelligent human centric lighting system 100. The client terminal 630 using this "spectral recipe" authoring platform can be distributed all over the world and can communicate with each other through the internet. The "light recipe sharing platform" connection in the cloud 610 of the present invention. Obviously, the present invention defines a "spectral recipe" creation platform here, that is, a "spectral recipe" creation platform means that a user or client terminal 630 can connect to the public cloud 6155 in the cloud 610 or a "light recipe sharing platform" through the internet, so that users or client terminal 630 can use the "spectral recipe" information on the public cloud 6155 or "light recipe sharing platform" for editing work. Therefore, after the user or client terminal 630 obtains various calculated usage experience data from the "sharing platform", the user or client terminal 630 can obtain the experience data based on the user's gender, age, race, season, time, etc., edit or create by client terminal 630 to construct an edited "spectral recipe" of multi-scene or multi-emotional light recipe.

Firstly, the first embodiment of the present invention uses the "spectral recipe" creation platform for commercial service and operation. For example, for the emotional stimulation result of 4,000K CCT, the user or client terminal 630 can combine different light scenes through the "spectral recipe" creation platform. For example, the first paragraph of client terminal 630 selects the light recipe of Maldives, the second paragraph is to choose the light recipe of Bali, and finally, the third paragraph ends with the light recipe on the beach of Monaco. In this way, after each segment is matched or configured with the spectral irradiation time, a new spectral combination of the multi-light scene can be formed. Finally, the spectral combination of the multi-light scene can be stored in the "sharing platform", which can provide other users with options. The spectral combination of this multi-light scene serves as the "spectral recipe" for its emotional adjustment. Among them, the creation platform of the present invention can also select a specific CCT at a specific time, for example, when a user wants to perform emotional stimulation at 9:00 am, for the circadian of the human body, the user can further select the aforementioned three light recipes at 9:00 am. Further, the multispectral irradiation time of each segment can be configured to be the same or different, for example, each segment is irradiated for 15 minutes. The first stage and the third stage may be arranged for 15 minutes, and the second stage may be arranged and irradiated for 30 minutes, and these same or different time configurations can be selected by the user.

Secondly, in the second embodiment of the present invention using the "spectral recipe" creation platform, different CCTs (that is, multiple emotions) can be combined to achieve emotion conversion through lighting with multiple emotions, for example, the client terminal 630 can use the "spectral recipe" creation platform to combine multiple emotions. For example, the client terminal 630 wanted to edit an emotion conversion from nervous to happiness, the first paragraph of the client terminal 630 is to select a light recipe of 4,000K (happy emotion), and the second paragraph is to select 3,000K (excited emotion). Finally, the third paragraph ends with a light recipe of 5,700K (amusement emotion). In this way, after each segment is matched or configured with multispectral irradiation time, a new multi-emotional light recipe can be formed. Finally, the light recipe of this multi-emotional emotion conversion can be stored in the "sharing platform", which can provide users with choices. This light recipe of multiple emotions serves as the "spectral recipe" for emotion adjustment or emotion conversion. Similarly, the creation platform in this embodiment can also select a specific CCT at a specific time. For example, when the user wants to perform emotional stimulation at 9:00 am, for the circadian of the human body, user can further select the above three paragraphs light recipe at 9:00 am. Further, the multispectral irradiation time of each segment can be configured to be the same or different, for example, each segment is irradiated for 15 minutes. The first stage and the third stage may be arranged for 15 minutes, and the second stage may be arranged and irradiated for 30 minutes, and these same or different time configurations can be selected by the user.

Next, it should be further explained that after the editing or creation of the above-mentioned first embodiment (light recipe of multi-light scenes) and the second embodiment (the combination of light recipe of multi-mood light scenes) is completed, step 430 also needs to go through step 430. Process to step 470. For example, after the client terminal 630 finishes the combination of light recipe of multi-mood, step 420 should be passed first, and the illumination should be performed through the combination of light recipe of multi-mood adjusted by a plurality of LED lamp group 621. Next, after step 430, it is determined whether the combination of the above-mentioned "spectral recipe" achieves the effect that the creator wants, including: the spectral combination of the multi-light scene of the first embodiment and the irradiation time of the corresponding configuration, and the second embodiment the multi-emotional light recipes and configured exposure times. If the effect set by the creator can be achieved, the lighting control parameters of the LED lamp group 621 construct these "spectral recipe" can construct a database, as shown in step 450. Wherein, the lighting control parameters includes color rendering (Ra), strobe, illuminance and CCT, etc. Then, as shown in step 470, after uploading the database of the lighting control parameters of the "spectral recipe" in step 450 to the cloud, these "spectral recipe" can be added to the public cloud 6155 of the present invention to form a light recipe sharing platform. If after step 430, it is determined that a certain "spectral recipe" cannot achieve the effect set by the creator, then you can go back to step 420 to adjust the irradiation time of each segment, or change to a different light scene combination (the first embodiment) or change different emotional combinations (the second embodiment), until these "spectral recipe" can achieve the effect set by the creator, then the process from step 430 to step 470 can be used to judge that these are effective. The "spectral recipe" of the light environment is added to the public cloud 6155 of the present invention to form a light recipe sharing platform.

In addition, in order to make the multi-scene combination or multi-emotion combination of the "spectral recipe" creation platform effective, it may be necessary to go through a specific LED lamp group 621 configured in the field and evaluated by a professional designer to achieve the best effect. Therefore, the present invention is further configured with a database of hardware services, as shown in step 4510, and further configured with a database of software services, as shown in step 4520. Among them, the database of hardware services and the database of software services are also embedded with some management information when building "spectral recipe", including installation or delivery of hardware devices, or including providing and building these "spectral recipe" through the database of software services software services such as space design, scene planning, or interface setting required by spectral recipe. In addition, the database of the hardware service and the database of the software service may be configured at one end of the client terminal 630, or may be configured in the cloud 610, which is not limited in the present invention. Obviously, in the embodiment of FIG. 4, the present invention has provided the process of constructing various "spectral recipe" and the database of "spectral recipe" construction services, as well as the hardware services required for the construction of "spectral recipe". The database and software service database have been established in the light recipe sharing platform. It should be noted that the "light recipe sharing platform" finally established in step 470 can provide "spectral recipe" that can provide effective spectral combinations for multi-light scenes and spectral combinations for multi-emotional light scenes. "Sharing platform" provides various commercial services and operations.

Figure 5A:
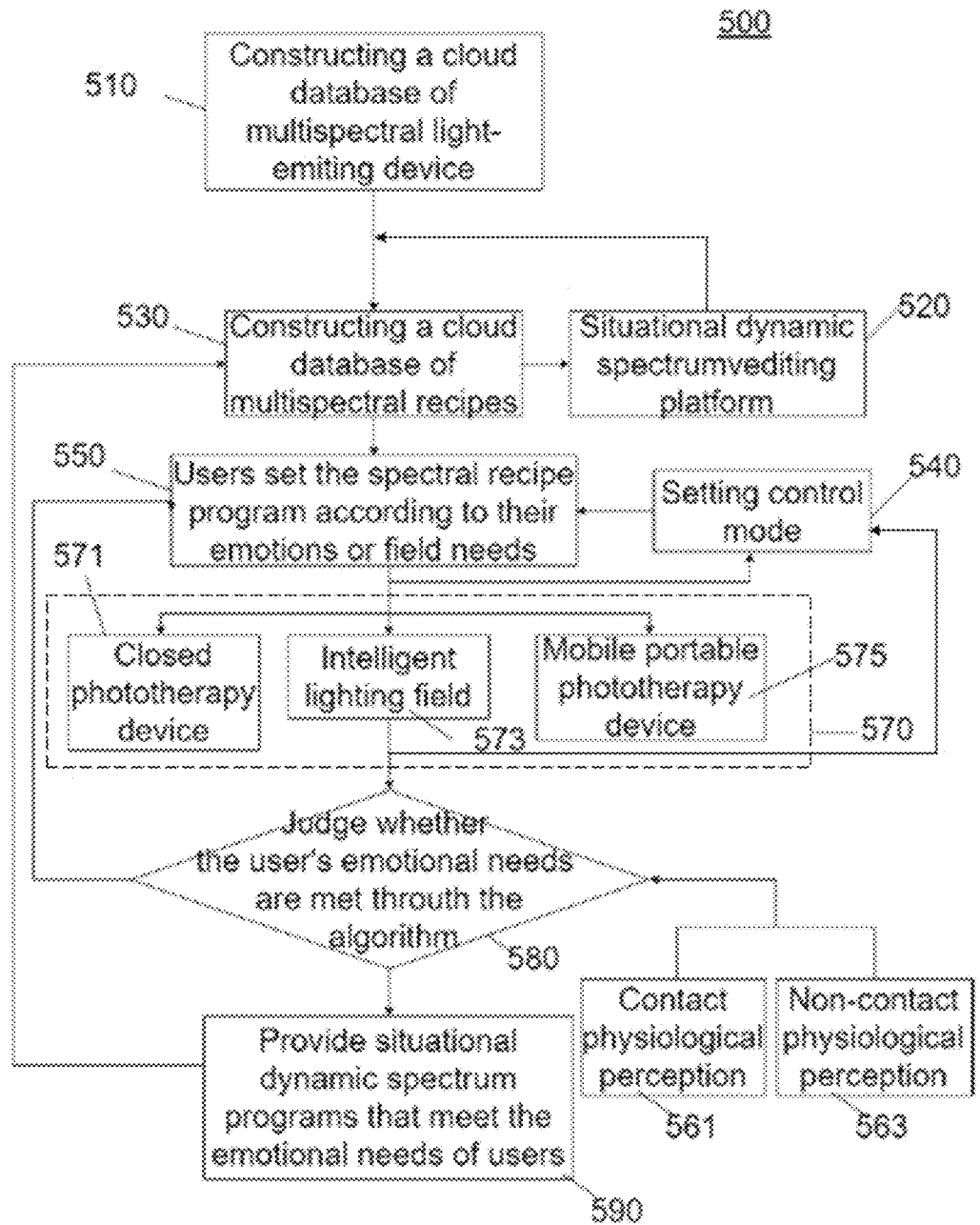
FIG. 5a is an automatically adjustable intelligent human centric lighting method of the present invention.

Next, please refer to FIG. 3 and FIG. 5a, FIG. 5a is an automatically adjustable intelligent human centric lighting method 500 of the present invention. First, as shown in step 510, construct a cloud database of multispectral light-emitting devices. The management control module 611 in the cloud 610 loads the "human centric lighting parameter database" stored in the memory module 617 or in the internal private cloud 6151 into the management control module 611. Among them, the "human centric lighting parameter database" stored in the cloud 610 already knows that various CCTs can make people (or users) get corresponding emotional stimulation. The management control module 611 loads the "human centric lighting parameter database" stored in the memory module 617 into the management control module 611. Among them, the "human centric lighting parameter database" stored in the memory module 617 already knows that various CCTs can give people (or users) corresponding emotional stimulation. For example, in Table 6, a specific CCT can make a specific emotion have the stimulating effect of additive reaction.

Next, as shown in step 530, a cloud data database of multispectral recipe for human centric lighting is constructed. In step 530, the "spectral recipe" stored in the "sharing platform" established in step 470 can be downloaded by the management control module 611 as a cloud data database source for constructing a multispectral recipe with human centric lighting in the present invention. Therefore, the process of forming the "spectral recipe" established in step 470 will not be described in detail, please refer to the detailed description of step 410 to step 470 in FIG. 4.

Next, as shown in step 520, a "situational dynamic spectrum editing platform" is provided. Similarly, the present invention defines a "situational dynamic spectrum editing platform" here, which is similar to the aforementioned "spectral recipe creation platform". The client terminal 630 can connect to the public cloud 6155 or "light recipe sharing platform" in the cloud 610 via the internet, so that the user or client terminal 630 can use the "spectral recipe" information on the public cloud 6155 or "light recipe sharing platform" for situational editing work. After the "situational dynamic spectral editing platform" obtains a variety of "spectral recipe" data from the "light recipe sharing platform", the "situational dynamic spectral editing platform" can edit or create the "spectral recipe" through the software application to construct an edited "situational dynamic spectrum program" that achieves (or satisfies) a specific emotional effect. This "situational dynamic spectrum program" can also be uploaded to the external private cloud 6153 in the cloud 610 and public cloud 6155, forming a database of "situational dynamic spectrum programs" that achieve (or satisfy) specific emotional effects.

Next, the editing process of the "situational dynamic spectrum program" in step 520 is described in detail. Please refer to FIG. 5b, which shows the editing process of the situational dynamic spectrum editing platform of the present invention. As shown in step 5210, the client terminal 630 downloads the "spectral recipe" stored in the "sharing platform" established in step 470 to the editing device used by the client terminal 630 through the internet to the management control module 611 in the cloud 610, for example, the editing device can be a computer or a smartphone or a workstation, one or more "spectral recipe" is connected to the software as a service (SaaS) or platform as a service (PaaS) configured in the cloud 610 through the editing device of the client terminal 630 in the system, afterwards, as shown in step 5220, through the SaaS or PaaS system configured on the cloud, set the lighting parameters of a specific CCT (that is, a specific mood) for the downloaded "spectral recipe", wherein the setting items of the lighting parameters of the light recipe include the generation time of the spectrum, the latitude and longitude of the spectrum, the brightness of the spectrum, the contrast of the spectrum, the flicker frequency of the spectrum, color rendering (Ra), etc., can be adjusted and set, and the above-mentioned adjustment methods are the same as the aforementioned methods of the present invention, including, replacing the "spectral recipe" in order of light scenes, or replace the light scene in the "spectral recipe", or delete a specific light scene in the "spectral recipe", or add a new light scene in the "spectral recipe", etc., because these adjustment methods are all has already been explained, so it will not be repeated here. For example, when the user downloads a spectral combination of a multi-light scene as the "spectral recipe" for emotional adjustment of happiness (4,000K), the multispectral brightness and the multispectral contrast can be finely adjusted, and the spectral flicker frequency in the second-stage Bali light recipe can also be adjusted at the same time, and the lighting sequence or lighting time of the aforementioned three-stage light recipe can also be adjusted or consider the latitude and longitude of the spectrum or the light recipe provided by the time of day, for example, add a light recipe at 4,000K CCT in Cannes, France, or delete the beach in Monaco through a SaaS or PaaS system. The light recipe above is changed to the light recipe at 4,000K CCT in Miami Beach, USA. For example, when the user or client terminal 630 downloads a "spectral recipe" for a spectral combination of a multi-light scene, and uses the SaaS or PaaS system to perform the combination of other light scenes, the above adjustment and change process can also go to step 510 that the "human centric lighting parameter database" stored in the memory module 617 is used to combine other emotions (CCT). For example, in the "spectral recipe" of the aforementioned happiness, excited, and joyful multi-light scenes, add the CCT of the fourth paragraph of the serene mood is used as the end stage of the lighting.

Next, as shown in step 5230, the relationship between the context function and the "spectral recipe" is edited. In step 5230, the "spectral recipe" that has been adjusted or set in step 5220 is edited in relation to the specific context function that the user or client terminal 630 wants to achieve, wherein, the relationship is divide the specific situational function you want to achieve into multiple blocks, and each of these blocks corresponds to a light scene in the "spectral recipe", for example, in step 5210, the user downloads a "spectral recipe" for a happy, excited and amusement multi-light scene, and when the user or client terminal 630 finally wants to achieve a good situational effect in the conference room (wherein, The so-called good conference situation effect, for example, the client terminal 630 chooses to be in the conference process, hoping that all the participants can stay relaxed at the beginning, stay focused during the discussion, and stay happy at the conclusion). The original "spectral recipe" can be adjusted to the "spectral recipe" of multi-light scenes such as relaxation, concentration and amusement through step 5220, and in step 5230, the user or client terminal 630 divides the meeting process into openings, discussing and conclusion three situational blocks, and then, the three situational blocks of opening, discussion and conclusion are corresponding to the "spectral recipe" of multi-light scenes of relaxation, concentration and amusement, so that the whole meeting can be the context of the process is linked to the "spectral recipe" of the multi-light scene in the conference room. Next, as shown in step 5240, after the user or client terminal 630 completes the "spectral recipe" correlation between the context of the conference process and the multi-light scene, and then adds "time setting" to the context block, it can complete a "situational dynamic spectrum program" with the function of conference situation, for example, setting the time for the opening, discussing and conclusion of the meeting to 5 minutes, 15 minutes and 10 minutes, as shown in FIG. 5c, can complete the "situational dynamic spectrum program with meeting context function". Finally, upload the "situational dynamic spectrum program" with the function situation to the cloud database. Obviously, the "situational dynamic spectrum program" obtained through the editing process in FIG. 5b can be stored in the memory module 617 or the external private cloud 6153 or the public cloud 6155 through step 530. Afterwards, these "situational dynamic spectrum programs" stored in the external private cloud 6153 can be provided for their own use as "situational dynamic spectrum programs" with automatically adjustable and intelligent human centric lighting. For example, when the user or client terminal 630 chooses to use a conference "situational dynamic spectrum program", the spectrum in the conference room can be automatically adjusted during the conference. Of course, the conference "situation dynamic spectrum program" edited by the client terminal 630 can also be stored in the public cloud 6155, so that business activities that are opened to other users through the cloud 610 can be achieved. Obviously, at this time, in step 530, in addition to the various "spectral recipe" downloaded from step 470, it also includes "situational dynamic spectrum programs", therefore, it can be stored in the cloud database established in step 530. Provide users with human centric lighting. In addition, it should be emphasized that in this embodiment, the editing of the "situational dynamic spectrum program" of multi-light scenes includes a combination of multi-light scenes with a single emotion and a combination of multi-light scenes with multiple emotions. Of course, it also includes the specific emotions in the multi-light scene combination can also be combined using the multi-light scene, which is not limited in the present invention.

Figure 5B:
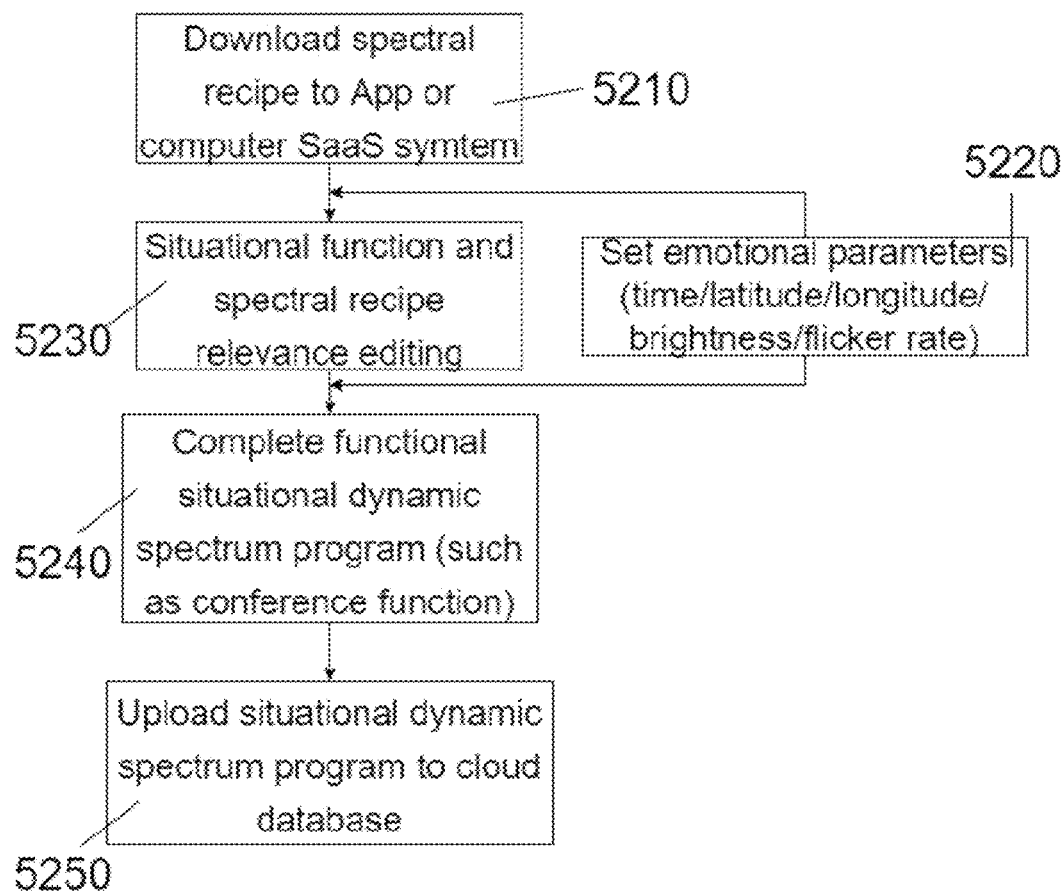
FIG. 5b is an editing process of the situational dynamic spectrum editing platform of the present invention.
Figure 5C:
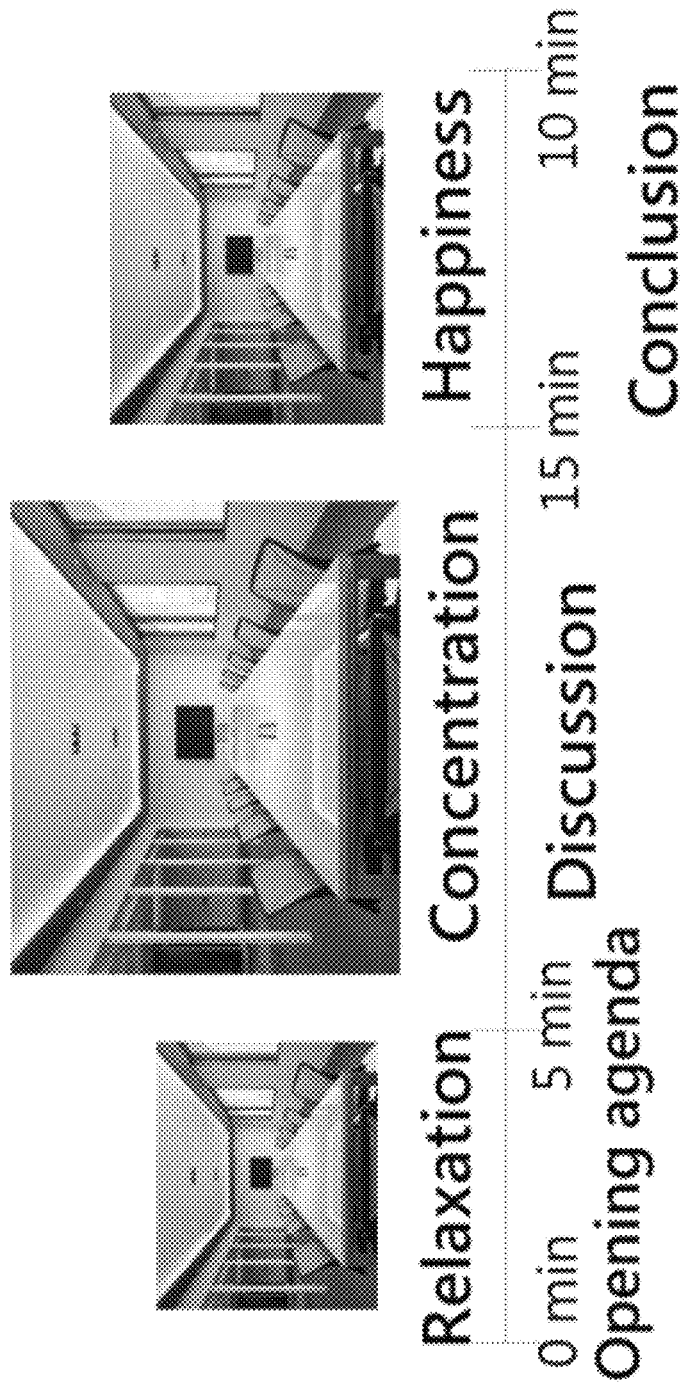
FIG. 5c is a kind of situational dynamic spectrum program with conference function of the present invention.

In addition, in the editing process of FIG. 5b above, another embodiment can also be selected, that is, the client terminal 630 downloads the "spectral recipe" stored in the "sharing platform" established in step 470 to the editing device used by the client terminal 630 through the internet to the management control module 611 in the cloud 610, and then, the user or client terminal 630 can select to edit the desired special situation setting function through SaaS or PaaS system (that is, first distinguish multiple blocks of specific situation functions), and then associate the desired special situation setting with the downloaded "human centric lighting parameter database", so as to complete the correlation editing between multiple situation blocks and corresponding emotions (CCT), so as to form a multi emotional multi light scene combination. For example, the editor has first divided the meeting process into three blocks: opening, discussing and conclusion, and then went to the "human centric lighting parameter database" stored in the memory module 617 to select the "spectral recipe" corresponding to the multi light scene formed by the corresponding emotions such as relaxation, concentration and amusement, or select the corresponding amusement "spectral recipe" for focused and relaxed multi light scenes. Since the way of travel relevance editing is the same, it will not be repeated in this embodiment.

Next, the present invention provides another preferred embodiment of an automatically adjustable intelligent human centric lighting method. Since the "situational dynamic spectrum program" constructed in step 530 is the result obtained by editing by individual client terminals 630, in order to achieve better effects, it is necessary to consider the light stimulation effects of different users on the "spectral recipe", and/or need to consider whether the lighting hardware configuration in different fields can achieve the light stimulation effect of "spectral recipe", which need to be adjusted.

Next, as shown in steps 550 and 570, the user or editor adjusts the lighting parameters in the "situational dynamic spectrum program" in order to meet emotional needs or emotion conversion. First, the user or client terminal 630 has downloaded a "situational dynamic spectrum program" from the external private cloud 6153 or public cloud 6155, for example, a "situational dynamic spectrum program" download in step 530. Wherein, this "situational dynamic spectrum program" can be a "spectral recipe" for a multi-emotional and multi-light scene, or a "spectral recipe" for a multi-light scene with a single emotion. Next, the user or client terminal 630 needs to set to be in a "specific environment" to execute the selected "situational dynamic spectrum program", wherein, in the embodiment of the present invention, the "specific environment" is divided into three types. The aspect, as shown in step 570, includes: a closed lighting system, an intelligent lighting field, and a portable human centric lighting device. When the "specific environment" is a closed lighting system, wherein the closed lighting system is a closed control room with multiple light-emitting devices 621 (such as a closed cavity that can isolate external light), it can It is provided that one or more users can receive the selected "situational dynamic spectrum program" in the closed cavity to perform the "spectral recipe" irradiation, as shown in step 571. In the process of spectral lighting, the present invention provides a function with control mode setting. For example, the multi-light scene can be controlled by the App on the mobile device used by the user or the client terminal 630 or the control module (such as the control device 670 with a monitoring panel) in the closed cavity, for example, under the influence of an environment with ambient light, the lighting parameters of the "spectral recipe" can be adjusted for the selected "situational dynamic spectrum program". The adjustment methods include time/longitude/latitude/brightness/flashing rate, etc., as shown in step 540. In addition, when the "specific environment" is an intelligent lighting field, the intelligent lighting field is a field with multiple light-emitting devices 621 that can accommodate multiple people, such as a conference room, a classroom, a kind of office place, a kind of social place, or a kind of factory, etc., so that multiple users can receive the "situational dynamic spectrum program" in the intelligent lighting field to perform "spectral recipe" lighting, as shown in step 573. In the process of spectral illumination, the controller, user or client terminal 630 of the field can control the selected "situational dynamic" through the application (App) on the mobile device used or the panel of the control device 670 in the field "spectral program" to adjust the light parameters of the "spectral recipe", for example, under the influence of an ambient light environment, or under the influence of the number of people in the field, to adjust the light parameters of the "spectral recipe", the adjustment methods include: time/latitude/longitude/brightness/flashing rate, etc., as shown in step 540. And, when the "specific environment" is a mobile portable lighting device, the mobile portable human centric lighting device is a virtual device related to the metaverse, such as: virtual reality (VR), mixed reality (MX) or an extended reality (XR) device, the user can accept the selected "situational dynamic spectrum program" through the virtual device to perform the "spectral recipe" irradiation, as shown in step 575. In the process of light recipe illumination, the user or client terminal 630 can adjust the light parameters of the "spectral recipe" through the App on the mobile device or the control module in the virtual device, for example, in an environment with ambient light. Under the influence, the light parameters of the "spectral recipe" can be adjusted for the selected "situational dynamic spectrum program", and the adjustment methods include time/latitude/longitude/brightness/flashing rate, etc., as shown in step 540.

Figure 6:
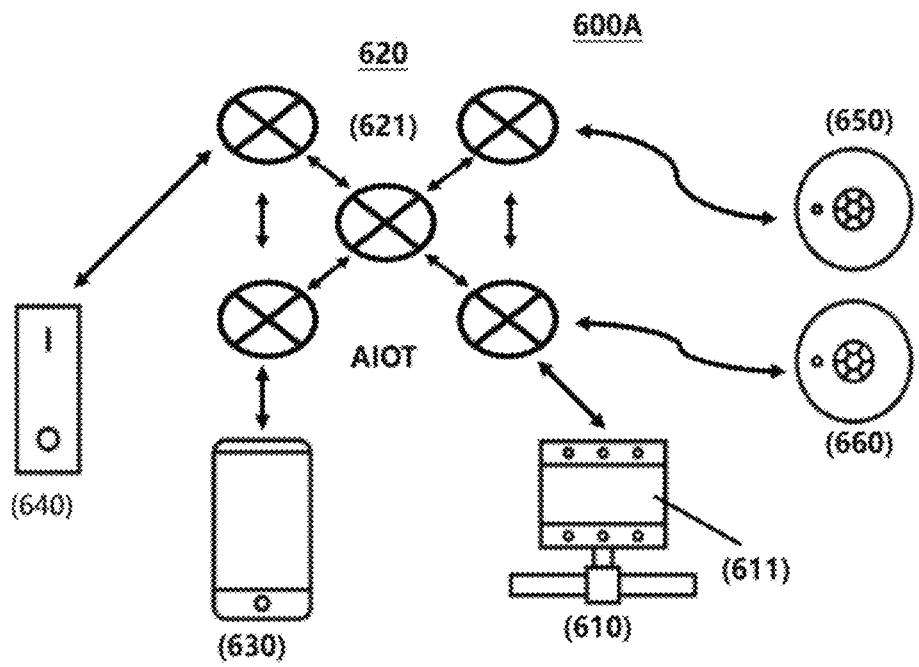
FIG. 6 is an intelligent human centric light system applied to commercial operation of the present invention.

During the operation of the above steps 540, 550 and 570, it is obvious that the default value of the "spectral recipe" is adjusted for the "specific environment" where the user is located. In the process of performing this default value adjustment, the ambient light information can be transmitted to the user or the user through the wireless communication device through the ambient light sensor 650 (as shown in FIG. 3 or FIG. 6) set in the "specific environment". It is an application (App) on the mobile device of the client terminal 630 or a control module in the "specific environment", which is used as a reference for adjusting the default value of the light parameters of the "spectral recipe". In addition, the occupancy sensor 660 (as shown in FIG. 3 or FIG. 6) set in the "specific environment" can also transmit the information of the number of people in the environment to the mobile device of the user or client terminal 630 through the wireless communication device. The occupancy sensor 660 can be a vibration sensor, and the frequency of vibration can be used to determine the number of people The occupancy sensor 660 may also be a temperature sensor, and the number of people is judged by the ambient temperature. In addition, the occupancy sensor 660 may also be a camera system, which judges the number of people through artificial intelligence (AI) face recognition. In addition, the occupancy sensor 660 can also be a gas concentration detector for detecting changes in the concentration of oxygen (O2) or carbon dioxide (CO2), to judge the effect of the user's spectral irradiation. When the temperature increases and the carbon dioxide (CO2) concentration also increases, it is judged that the spectral irradiation achieves the desired emotional effect. Obviously, through the operation of step 540, step 550 and step 570, a "situational dynamic spectrum program" that can be automatically adjusted the light parameters for intelligent human centric lighting can be formed. In particular, it should be noted that in order to ensure that the user can achieve the effect of changing emotions or emotion conversion during the process of intelligent human centric lighting, the light-emitting device 621 that performs lighting must be used in different specific environments or real-time monitoring and adjustment of the lighting parameters in the field to achieve specific effects.

The present invention then provides another preferred embodiment of an automatically adjustable intelligent human centric lighting method. It is to further provide some sensing devices to feedback whether the user achieves the required emotional effect after being irradiated by the "spectral recipe" of the "situational dynamic spectrum program". These sensing devices include contact physiological sensors (e.g., step 561) or non-contact optical sensors (e.g., step 563). Among them, the contact type physiological sensor is configured on each user to measure the user's heartbeat, blood pressure, pulse, blood oxygen concentration or electrocardiogram, etc., to determine whether the user meets the required emotion. The non-contact optical sensor can be configured in the light environment where the user is located to measure the illuminance, CCT, spectrum, color rendering index, etc.

As shown in step 580, judge whether the user's emotional needs are meet. After the user has performed the "spectral recipe" of the specific "situational dynamic spectrum program" in the "specific environment", an algorithm will be used to determine whether the current spectral irradiation process has reached the user's mood need. Wherein, the algorithm in step 580 may be a ratio of the signals between the user's physiological signals (including: heartbeat, blood pressure, pulse and respiration rate) obtained through an algorithm, and this ratio is used to determine whether the specific emotional needs are met. Therefore, after the calculation processing of the management control module 611, a database of physiological signal ratios relative to various emotions is established and stored in the memory module 617 in the cloud 610 or the internal private cloud 6151. for example, when the user is illuminated by the "situational dynamic spectrum program" of happy emotions for a period, the heartbeat, blood pressure and blood oxygen are getting back to the App on the mobile device or the "specific environment" through the contact physiological sensor in step 561. At this time, the App on the mobile device or the control module in the "specific environment" calculates a proportional value from the feedback data through an algorithm, and then transmits this proportional value to the management control module 611 through the internet, compare the ratio value stored in the memory module 617 or the internal private cloud 6151 through the management control module 611. For example, if the ratio value calculated by the algorithm falls between 1.1 to 1.15, and the management control module 611 determines that the probability of this ratio value reaching a happy mood is 80%, and the probability of reaching a happy mood is 20%. If we judge whether the probability of achieving the effect is 75%, the management control module 611 will judge that the user has reached the required happiness after lighting through the "spectral recipe" of the selected "situational dynamic spectrum program" and will stop the irradiation program after the "situational dynamic spectrum program" completes the irradiation program. Then, in step 590, the "spectral recipe" data of the current "situational dynamic spectrum program" is stored in the internal private cloud 6151, the external private cloud 6153 or the public cloud 6155 in the cloud 610. If it is judged that after the user is illuminated by the "spectral recipe" of the selected "situational dynamic spectrum program", the ratio value calculated by the algorithm has only a 50% probability of reaching the happy mood, which means that the happy mood required by the user has not yet been achieved. Currently, it is necessary to return to step 550, after adjusting the light parameters of the "spectral recipe" of the selected "situational dynamic spectrum program" through the control mode of step 540, perform the lighting program again, and pass the contact method of step 561. The physiological sensor gets back the user's heartbeat, blood pressure and blood oxygen to the App on the mobile device or the panel of the control device 670 in the field after the ratio calculated by the algorithm, and then transmits the ratio to the cloud database through the internet at a time and communicates with the cloud. The proportions in the database are compared until the desired happiness emotion is reached. Obviously, in the storage process of step 590, it will also be stored in step 530 at the same time, so at this time, in the cloud database established in step 530. In addition to the various "spectral recipe" downloaded from step 470, it also includes the "situational dynamic spectrum program" adjusted by the algorithm. Therefore, storing in the cloud database of the "situation dynamic spectrum program" established in step 530 can provide a more effective "situation dynamic spectrum program" for the user to perform human centric lighting. In addition, it should be emphasized that in this embodiment, the editing of the "situational dynamic spectrum program" of multi-light scenes includes a combination of multi-light scenes with a single emotion and a combination of multi-light scenes with multiple emotions. Of course, it also includes the specific emotions in the multi-light scene combination can also be combined using the multi-light scene, which is not limited in the present invention.

The intelligent human centric lighting system or method provided by the present invention can judge whether the user can judge or feel whether the effect has been achieved after the illumination of the "spectral recipe" selected by the user through the feedback signal. The solution provided by the present invention is to judge through the user's actual physiological signal. Therefore, the above embodiment of using physiological signals as an algorithm is only an example to let the public know the implementation of the technical means of the present invention, so it should not be a limiting condition of the present invention within the scope of rights. The invention should emphasize that the scope of the "algorithm" of the present invention is if the individual comparison is carried out through the user's physiological signals, or the data in the cloud 610 database is further compared after processing the physiological signals.

According to the above-mentioned intelligent human centric lighting method that can be automatically adjusted, the present invention further provides an intelligent human centric lighting system for commercial operation, as shown in FIG. 6. The intelligent human centric lighting system 100 for commercial operation of the present invention includes: a cloud 610, a management control module 611, a lighting field terminal 620 for intelligent lighting, and a client terminal 630. The devices configured in the lighting field terminal 620 include: a light-emitting device or LED lamp group 621, at least one occupancy sensor 660, at least one ambient light sensor 623, and a control module 640. The lighting field terminal 620 includes a "specific environment". According to FIG. 5*a*, the "specific environment" can be divided into three fields, including: a closed space that can be used by multiple people or an intelligent lighting field domain, as well as mobile portable human centric lighting devices for personal use or enclosed spaces.

First, FIG. 6 discloses an intelligent human centric lighting system 600A for commercial operation, which can be applied to an embodiment used by multiple people. The client can use the portable communication device to download the "spectral recipe" or "situational dynamic spectrum program" to the cloud 610 through the internet and use the portable communication device to activate the LED lamp group 621 for human centric lighting, in order to form an intelligent human centric lighting system that can be automatically adjusted. Wherein, in this embodiment, the client may be at the remote end, or may be at the specific environment end at the near end. When the client is remote, the internet is the Artificial Intelligence of Things (AIoT) formed by the Internet of Things (IoT) and Artificial Intelligence (AI). When the client is at the near end, the internet is a wireless communication protocol formed by a gateway, including Wi-Fi or Bluetooth.

When a plurality of users has been distributed in a closed space or intelligent lighting field, the portable communication device can carry out specific "spectral recipe" or "situational dynamic spectrum program" human centric lighting for the starting LED lamp group 621. The closed lighting system is a closed space with a plurality of light-emitting devices (for example, a closed cavity that can isolate external light), which can provide one or more users to receive human centric lighting in the closed cavity. The intelligent lighting field is a field with multiple light-emitting devices that can accommodate multiple people, such as a conference room, a classroom, an office, a social place or a factory, which can provide multiple users to receive human centric lighting in the intelligent lighting field.

In addition, the LED lamp group 621 can be further configured in a closed space or in an intelligent lighting field. When multiple users perform human centric lighting in the closed space, the closed space can provide a space that is isolated from external environmental interference, allowing users to immerse themselves in the selected "spectral recipe" or "situational dynamic spectrum program". At the same time, in order to enable people to achieve the desired effect faster due to lighting, the contact physiological sensor configured on each user can also be used to measure the user's heartbeat, blood pressure, pulse, blood oxygen concentration or electrocardiogram, etc., to determine whether the user has achieved the required emotion. In addition, face recognition can also be performed through the vibration frequency, ambient temperature, ambient carbon dioxide concentration detected by the occupancy sensor 660 and the background ambient light sensor 650 configured in the intelligent lighting field, and the ambient carbon dioxide concentration, spectrum, The light intensity, flashing rate, and CCT are transmitted to the management control module 611 in the cloud 610 through the Artificial Intelligence of Things (AIoT) for calculation, so as to determine whether the user has achieved the set effect. Similarly, in the process of spectral illumination, the "spectral recipe" of the multi-light scene can be adjusted through the App on the mobile device used by the client terminal 630 or the control module in the intelligent lighting field, for example, when the ambient light sensor When the 650 detects the influence of ambient light, it can adjust the "spectral recipe" of the selected "situational dynamic spectrum program". The adjustment methods include time, latitude and longitude, brightness, flashing rate, etc. show the operation process of step 540, step 550, step 570 and step 580 in FIG. 5*a*).

Next, FIG. 6 further discloses an embodiment of an intelligent human centric lighting system 600A for commercial operation as shown, applied to personal use. The user can use the portable communication device to download the "spectral recipe" or "situation dynamic spectrum program" to the cloud 610 through the internet and activate the mobile portable human centric lighting device through the portable communication device to perform human activities. Due to lighting, to form an intelligent human centric lighting system that can be automatically adjusted. Especially when the user has worn the portable human centric lighting device on the user's eyes, the portable communication device can be used to activate the LED lamp group 621 configured in the portable human centric lighting device. A specific "spectral recipe" or "situational dynamic spectrum program" for human centric lighting. Wherein, the portable human centric lighting device is a virtual device related to the metaverse, such as a Virtual Reality (VR), Mixed Reality (MX) or Extended Reality (XR) device, which can provide a single user receives human centric lighting through a virtual device.

In addition, in order to enable the human centric lighting of the mobile portable human centric lighting device to achieve the desired effect faster, the contact type physiological sensor configured on the user's body can also be used to measure the user's heartbeat, blood pressure, pulse, blood oxygen concentration or electrocardiogram, etc., to determine whether the user has the required emotion. Similarly, in the process of spectral irradiation, the "spectral recipe" of the multi-light scene can be adjusted through the App on the mobile device used by the client terminal 630 or the control module in the closed cavity (for details, please refer to step 540, step 550, step 570 and step 580 during the operation).

In a preferred embodiment, the configuration of the LED lamp group 621 can be configured according to the customized requirements through the hardware service database of step 4510 and the software service database of step 4520. Finally, the portable communication device in the automatic adjustable intelligent human centric lighting system of the present invention can be an intelligent phone, a tablet device or a workstation. The portable communication device can download an application (APP) containing intelligent human centric lighting from the Artificial Intelligence of Things (AIoT) to the management control module 611. Through this app, the user can connect with the public cloud in the cloud 610, and then select the desired "spectral recipe" or "dynamic spectrum program" from the public cloud for human centric lighting. At the same time, through this app, the LED lamp group 621 can also be remotely turned on or off through the short-range communication protocol, to control the spectrum to achieve the effect of human centric lighting. Among them, if the user confirms that those "spectral recipe" or "situational dynamic spectrum programs" are effective, he can download these "spectral recipe" or "situational dynamic spectrum programs" to the portable communication device of the client, and then configure the switching device 640 of the client, You can directly open the "spectral recipe" or "situational dynamic spectrum program" for human centric lighting without internet connection, which allows users to quickly enter the human centric lighting program.

The above-mentioned intelligent human centric lighting system that can be adjusted automatically is to establish a database of the brain's "blood oxygen-level dependent response increase" condition through the intelligent human centric lighting system. After the database is edited by the spectral recipe, a cloud database of multispectral light-emitting devices is constructed. The cloud database can provide users to set the emotional needs of the brain to be achieved in the intelligent human centric lighting system, and the intelligent human centric lighting system can judge or suggest the light recipe to closed human centric lighting device, the open lighting field or the movable human centric lighting device. After that, when the user experiences the light situation, the intelligent human centric lighting system algorithm is used to determine the user's physiological and psychological state. If the emotional needs of the brain have not been fulfilled, the "spectral recipe" program will be continuously modified through the feedback signal of the wireless device, and after re-adjusting the "spectral recipe", it will be re-verified whether the expected emotional needs have been met. If the brain reaches the emotional needs, it will provide a "spectral recipe" or "situational dynamic spectrum program" formed by lighting that meets the user's emotional needs to carry out the lighting process. Obviously, the intelligent human centric lighting method and system disclosed by the present invention can make the human centric lighting effect of the emotional needs of the brain can be commercialized and benefit more users without the need to use fMRI.

Figure 7:
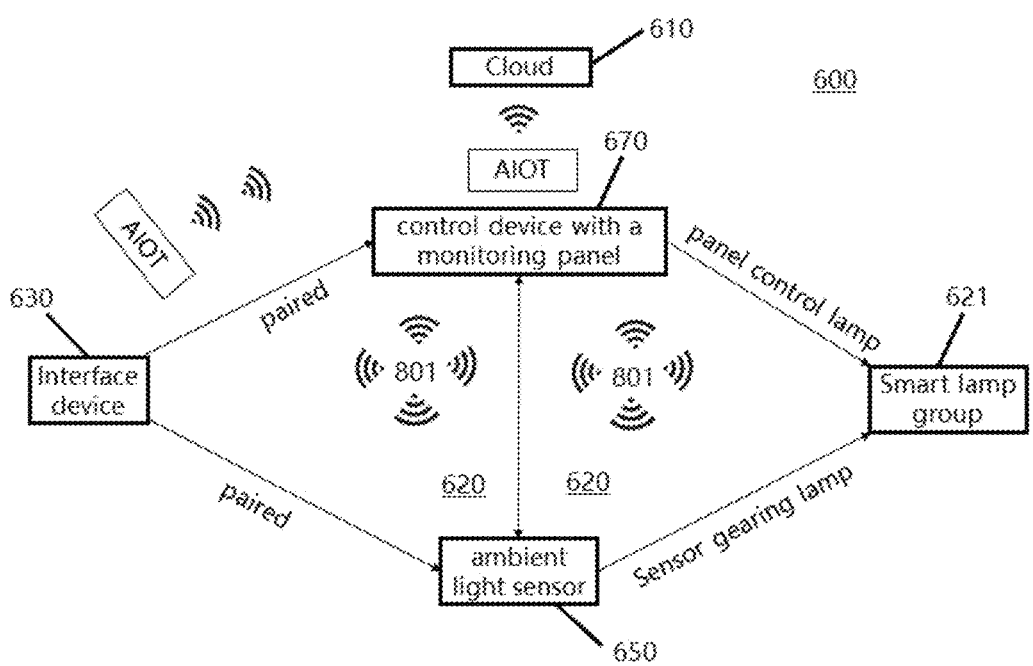
FIG. 7 is a lamp group control architecture of the intelligent human centric lighting system in FIG. 6 at the lighting field end of the present invention.

Next, please refer to FIG. 7, which further discloses the lamp group control architecture of the intelligent human centric lighting system in FIG. 6 at the lighting field end of the present invention. First, as shown in FIG. 7, the lighting field 620 of the intelligent human centric lighting system 600 is a closed field or space, and in the lighting field 620, some lamp groups 621 may have been configured. Wherein, in the present embodiment, the lamp group 621 is an intelligent lamp group with communication function (smart lamp group for short). In the embodiment, the smart lamp group 6211 can be a single lamp, or it can be composed of multiple lamps. Next, the ambient light sensor 650 is disposed in the lighting field 620. Wherein, the quantity of the ambient light sensor 650 may be one or more, depending on the quantity of the smart lighting group 621 configured. Moreover, these ambient light sensors 650 are equipped with communication modules, which can be paired with the smart lamp group 621 through the communication protocol 801 such as Zigbee, Bluetooth or WIFI. The pairing described here refers to connecting an ambient light sensor 650 with a smart lamp group 621 through the communication protocol 801 such as Zigbee, Bluetooth or WIFI, so that the smart lamp group 621 can be connected or paired with ambient light sensor 650 controls the spectrum of the light it illuminates. Wherein, the smart lamp group 621 may be composed of multiple smart lamps.

Figure 8A:
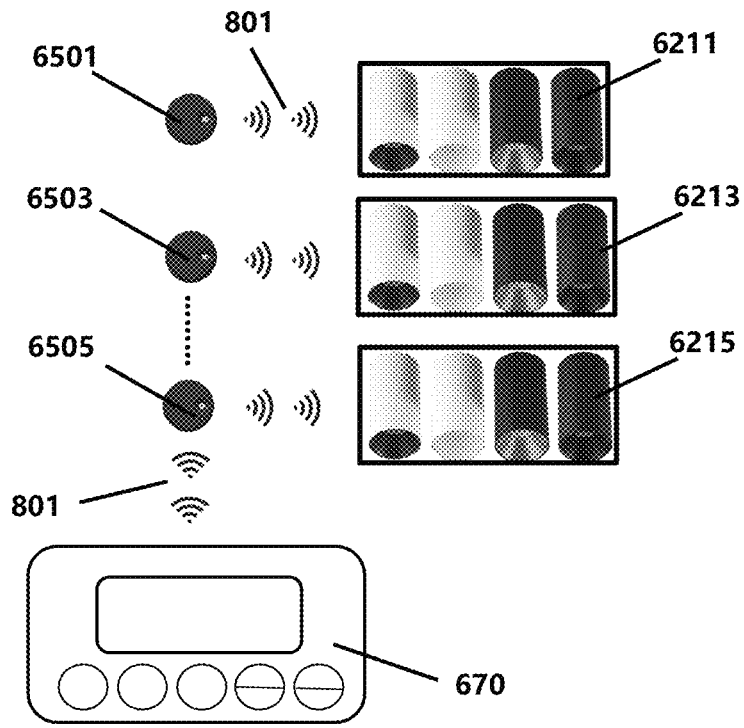
FIG. 8a, it is a schematic configuration diagram of the present invention for controlling the illumination of the smart lamp group in the lighting field.

Further, in the following embodiments of the present invention, one ambient light sensor 650 can be connected or paired with multiple smart lamp groups 621 to form a single ambient light sensor 650 to control the lighting spectrum of the multiple lamp groups. As shown in FIG. 8a, it is a schematic configuration diagram of the present invention for controlling the illumination of the smart lamp group in the lighting field. As shown in FIG. 8a, multiple ambient light sensors (6501, 6503, 6505) are paired respectively one by one with multiple smart lamp groups (6211, 6213, 6215). For example, an ambient light sensor 6501 is used to connect or pair with a smart lamp group 6211 composed of multiple lamps, so the multiple lamps in the smart lamp group 6211 can be controlled by an ambient light sensor 6501. Smart lamps illuminate with the same "spectral recipe". According to the above, the preferred embodiment of the ambient light sensor 650 of the present invention is a sensing chip that can provide constant illuminance, and the sensing chip includes an illuminance sensor and an LED drive circuit.

Figure 8B:
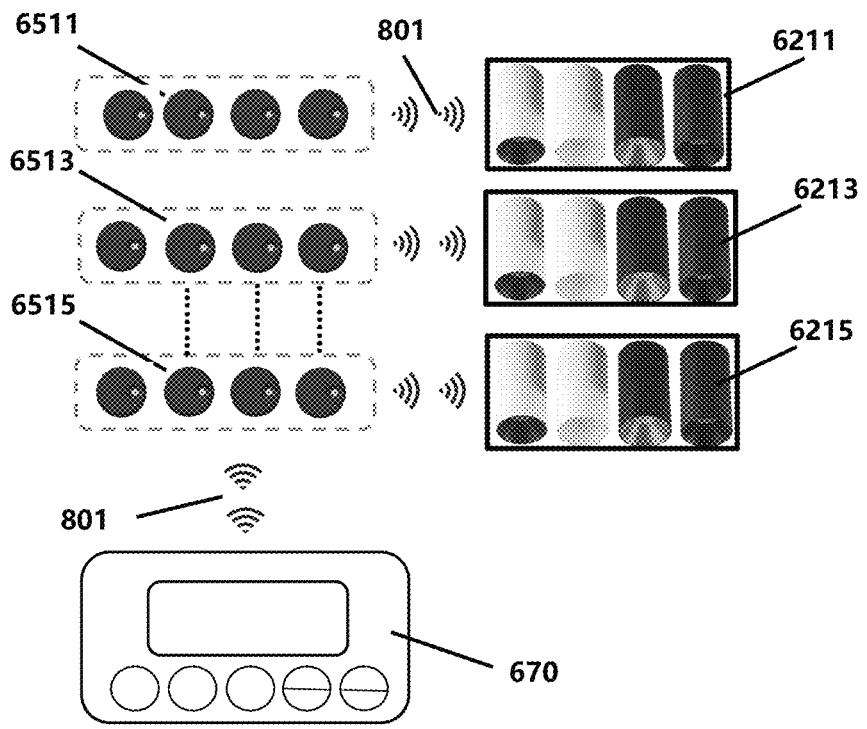
FIG. 8b, it is another schematic configuration diagram of the present invention for controlling the illumination of the smart lamp group in the lighting field.

In addition, in another embodiment, multiple ambient light sensor modules (6511, 6513, 6515) and multiple smart lamp groups (6211, 6213, 6215) can also be connected via Zigbee, Bluetooth or WIFI communication protocols 801 forming a connection or pairing. As shown in FIG. 8b, it is another schematic configuration diagram of the present invention for controlling the lighting of a smart lamp group in the lighting field. As shown in FIG. 8b, each ambient light sensor modules (6511, 6513, 6515) is composed of multiple ambient light sensors. When ambient light sensor modules (6511, 6513, 6515) are connected or paired with multiple smart lamp groups (6211, 6213, 6215). Ideally, an ambient light sensor in each ambient light sensor module 6511 is paired with an intelligent lamp in a smart lamp group 621, and an ambient light sensor can be used to control the intelligent lamp to illuminate with the same "spectral recipe". Obviously, the present invention does not limit the number of connection or pairing between the ambient light sensor 650 and the smart lamp group 621.

Then, for convenience, the user can adjust the lighting parameters of the lighting spectrum of the smart lamp group 621 in the lighting field 620. The present invention further provides a control device 670 with a monitoring panel, wherein the control device 670 can be the mobile device 630 used by the user in FIG. 6 or the control module 640 disposed in a closed cavity. Wherein, the control device 670 can be configured or fixed in the lighting field 620.

The control device 670 in this embodiment is a control device 670 with a display function and a communication function. The control device 670 can form a connection with the ambient light sensor 650 through the communication function, so that the connection or pairing result between the ambient light sensor 650 and the smart lamp group 621 can be stored in the control device 670. Therefore, the control device 670 can control the light spectrum of the smart lamp group 621 through the ambient light sensor 650. In addition, the control device 670 in this embodiment can also be directly connected or paired with the smart lamp group 621 through the communication function. Therefore, the control device 670 can directly control the light spectrum of the smart lamp group 621 according to the needs of users. The connection or pairing of the control device 670 with the ambient light sensor 650 and the smart lamp group 621 is accomplished through the communication protocol 801, such as the Zigbee, Bluetooth or WIFI arranged in the confined space of the lighting field 620. Therefore, when the control device 670 wants to control the smart lamp group 621 to provide the light spectrum, it is also done through the communication protocol 801, such as the Zigbee, Bluetooth or WIFI. As the foregoing mentioned above, in addition to the communication module (not shown in the figure), the ambient light sensor 650 disclosed in the present invention is further configured with an illumination detection module (not shown in the figure). These detected light environment conditions can be transmitted to the control device 670 through the communication protocol 801, such as the Zigbee, Bluetooth or WIFI.

After the ambient light sensor 650, the smart lamp group 621 and the control device 670 arranged in the lighting field 620 have been paired through the communication protocol 801, such as the Zigbee, Bluetooth or WIFI, the present invention further discloses a user-used mobile communication device is used as the interface device 630 between the cloud 610 and the lighting field 620. Wherein, the interface device 630 includes a smart phone, a personal digital assistant (PDA) or a notebook computer (NB). The interface device 630 can be used through an application program (App) in a smart phone or a notebook computer (NB) to connect a software as a service (Software as a Service, SaaS) or a platform as a service (platform as a service, PaaS) system program to complete the connection and paring between the interface device 630 and the ambient light sensor 650 and the control device 670. The user interface (UI) can be seen through the interface device 630, and the user interface (UI) of the interface device 630 can be operated to control the spectrum of its illumination through the ambient light sensor 650. Wherein, the interface device 630 and the ambient light sensor 650 and the control device 670 can also choose to use the Zigbee, Bluetooth or WIFI communication protocol 801 to complete the pairing. Therefore, when the ambient light sensor 650 detects the influence of ambient light or background light, the interface device 630 or the control device 670 can control the selected "situational dynamic spectrum program" or "settings related to circadian rhythm" through the cloud 610 to adjust the "spectral recipe" including time, latitude and longitude, brightness, flicker frequency, etc. Please refer to the operation process of step 540, step 550, step 570 and step 580 shown in FIG. 5a for details adjustment method. Wherein, both the interface device 630 and the control device 670 can communicate with the cloud 610 through the Artificial Intelligence of Things (AIoT). Obviously, in the control structure of the lighting field 620 of the intelligent human centric lighting system of the present invention, the smart lamp group 621 can be controlled through the mobile phone 630, the ambient light sensor 650 or the monitoring panel of the control device 670. The present invention allows the user to operate or control the lighting of the field 620 conveniently.

Figure 9:
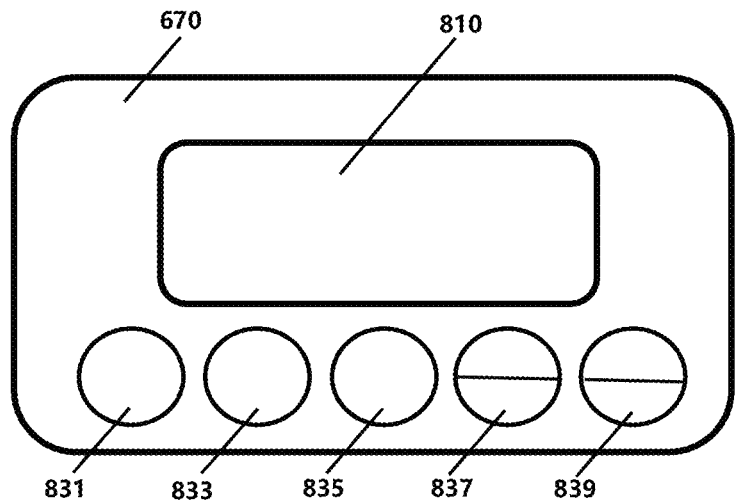
FIG. 9 is a control device with display and communication functions of the present invention.

Next, please refer to FIG. 9, which is a control device with display and communication functions according to the present invention. As shown in FIG. 9, firstly, from the appearance, the control device 670 can be selected to be a geometric shape. For example, in this embodiment, a rectangular structure is selected, especially a rectangular structure with a golden ratio (16:9). Wherein, the length of the long side is 100 mm to 150 mm. Next, the control device 670 configures a display 810 near the central area to display the digital signals of the lighting parameters of the ambient light sensor 650 and the smart lamp group 621 in the lighting field 620. In the area below the display 810, a plurality of operation buttons is arranged. Wherein, the button 831 is a kind of overview button, which can view all the values of the ambient light sensor 650 and can also be used as a function key to switch parameters. The button 833 is a selection (or switching) button, which can sequentially display the dynamic information of the current ambient light detected by each ambient light sensor 650. Button 835 is a switch button of the lighting parameters, which can be selected or switched to the lighting parameters that the user wants to display in sequence, including illuminance (lx), Correlated Color Temperature (CCT), color rendering (Ra), equivalent melanopic illuminance (EML), circadian action factor (CAF), light flicker frequency and/or other information. The button 837 is a button for adjusting illuminance, which can be used to adjust the illuminance of the smart lamp group 621 paired with the selected ambient light sensor 650, for example, adjust the illuminance up or down through the button 837. Button 839 is a CCT adjustment button, which can adjust the CCT of the intelligent lamp group 621 paired with the selected ambient light sensor 650, for example, adjust the CCT up or down through the button 839.

Wherein, the main calculation principle of the above-mentioned equivalent melanopic illuminance (EML) is to multiply the vertical visual illuminance in a space by the ratio of the light source. Therefore, the melanopic illuminance (EML) measures the level of light in a field that stimulates the human body's physiological cycle. It is used to quantify the biological effects of light on people, and it is also one of the standards recommended by the international WELL building standard for planning human centric lighting. Therefore, different daily activities are suitable for different EML values. For example, during the day or when you need to focus, you need a high EML value; on the contrary, at night or when you need to relax, you need a low EML value. Therefore, when the intelligent human centric lighting system 100 of the present invention is activated, the control device 670 can reset the EML value according to the time of day. For example, the highest and lowest values of the EML value are set according to the current time. When the EML value detected by the ambient light sensor 650 reaches the highest and lowest values, the control device 670 will send out information including different sounds or displays screens of different colors. Wherein, in the embodiment of the present invention, the indoor vertical visual EML value in the daytime is set to 250-500, the indoor vertical visual EML value in the evening time is set to 100-150, and the indoor vertical visual EML value in the evening time is set to 50~75.

In addition, the above-mentioned Circadian Action Factor (CAF) is mainly calculated based on the illuminance of the light of the smart lamp group 621 and is used to measure the stimulation level of the lamp to the human body. For example, when the circadian action factor (CAF) value is higher, the light stimulates the human body's physiology more highly, which can make people energetic. The lower the CAF value, the lower the stimulation of light to the human body, which makes people feel relaxed. Therefore, the control device 670 can set the CAF value according to the user's personal circadian rhythm. For example, during the period from 9 am to 11 am, the control device 670 sets a "spectral recipe" with a CCT of 5700K and CAF=0.8 and can simultaneously set the upper limit value (for example is 1) and the lower limit value of CAF (for example is 0.6). Therefore, when the CAF value detected by the ambient light sensor 650 reaches the highest and lowest values, the control device 670 will send out information including different sounds or display screens of different colors.

Obviously, the difference between CAF and EML is that the former measures the stimulation of the light spectrum of the intelligent lamp group 621 to the human body, while the latter measures the stimulation of the field to the human body. But the same thing is that the higher the value, the higher the stimulation to the human body can boost the spirit; the lower the value, the lower the stimulation to the human body can help relax the body and mind.

In addition, multiple ambient light sensors (6501, 6503, 6505) or multiple ambient light sensor modules (6511, 6513, 6515) in FIG. 8a and FIG. 8b are all connected via Zigbee, Bluetooth or WIFI communication protocol 801 is paired with the control device 670. Therefore, after the control device 670 downloads a specific "spectral recipe" to the cloud, the "spectral recipe" can be transmitted to multiple ambient light sensors (6501, 6503, 6505) through the communication protocol 801, such as the Zigbee, Bluetooth or WIFI, or multiple ambient light sensor modules (6511, 6513, 6515). Afterwards, multiple ambient light sensors (6501, 6503, 6505) or multiple ambient light sensor modules (6511, 6513, 6515) are used to control the smart lamp group (6211, 6213, 6215) according to the "spectral recipe" to provide the lighting.

Since the intelligent human centric lighting system 100 disclosed in the present invention is a commercialized system with practical effects, it is necessary to control the various lighting parameters in the lighting field 620 very precisely, including at least illuminance (lx), Correlated Color Temperature (CCT), color rendering (Ra), equivalent melanopic illuminance (EML), circadian action factor (CAF), light flicker frequency and/or other information. In particular, the equivalent melanopic illuminance (EML) and circadian action factor (CAF) in the light field 620 must be accurate, in order to determine the effect of the "spectral recipe" used by the user on emotional adjustment. Therefore, the present invention further detects various background light sources in the control light field 620, especially the light that overflows into the space through the windows of the building and compares the influence of the target spectrum set in the light field 620 to compensate so that the lighting field 620 can be maintained in the environment of the target spectrum.

Next, the present invention discloses an intelligent human centric lighting system with automatic adjustment of space lighting parameters and its method. As shown in FIG. 10a to FIG. 10d, they are schematic diagrams showing some embodiments in which an external light source enters a space where an intelligent human centric lighting system is configured. First, a plurality of ambient light sensors 650 are arranged in the space 620, and there is a plurality of openings 623 on one side of the space 620, allowing external light to enter the space 620. Wherein, the opening 623 may be a window or a door. The external light can be sunlight during the day, moonlight or neon lights at night. The intelligent human centric lighting system 100 arranged in the space 620 may be the intelligent human centric lighting system shown in FIG. 3, FIG. 6 or FIG. 7, which is not limited by the present invention. In addition, in order to clearly illustrate the intelligent human centric lighting system and its method with automatic adjustment of lighting parameters in the space, the intelligent human centric lighting system 600 shown in FIG. 7 is taken as an example for illustration.

Figure 10A:
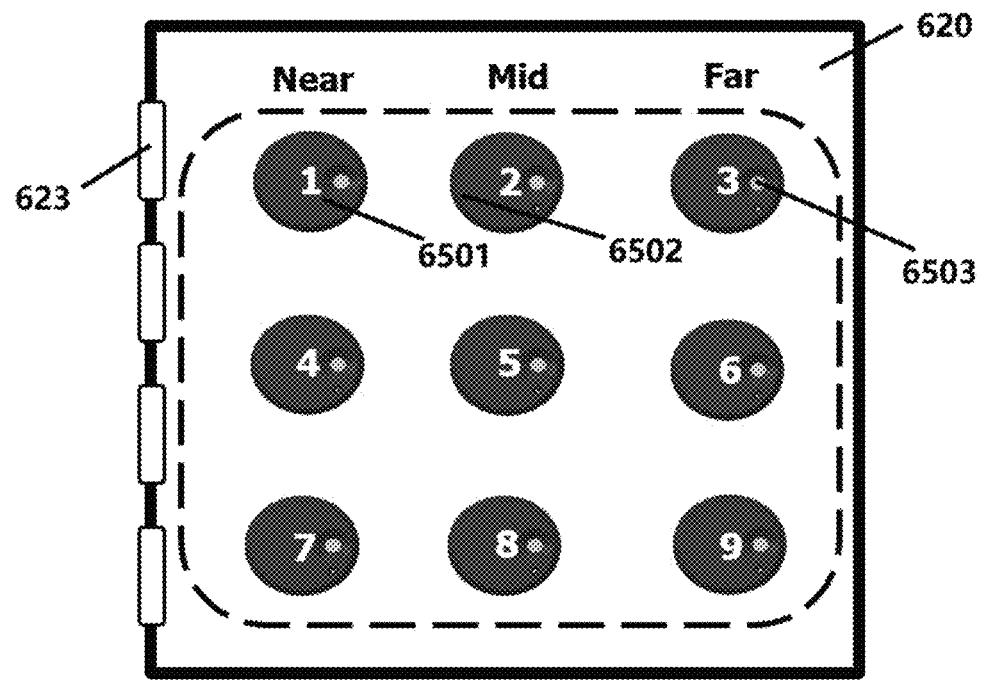
FIG. 10a, FIG. 10b, FIG. 10c and FIG. 10d are schematic diagrams showing some embodiments of the present invention in the space where an external light source is injected into a space equipped with a smart human-caused lighting system.
Figure 10B:
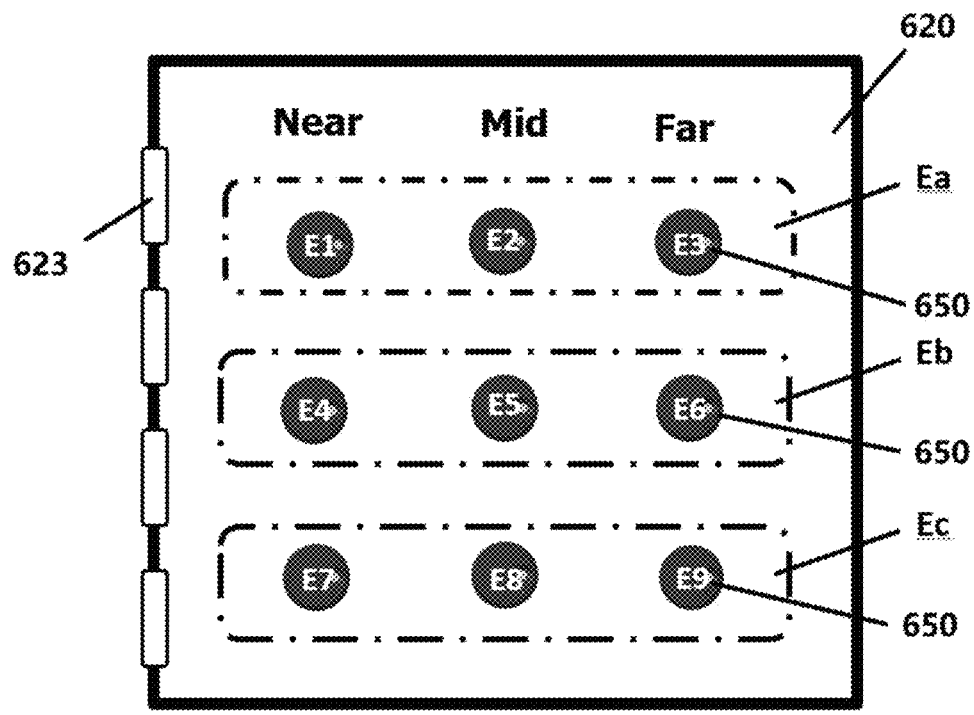
Figure 10C:
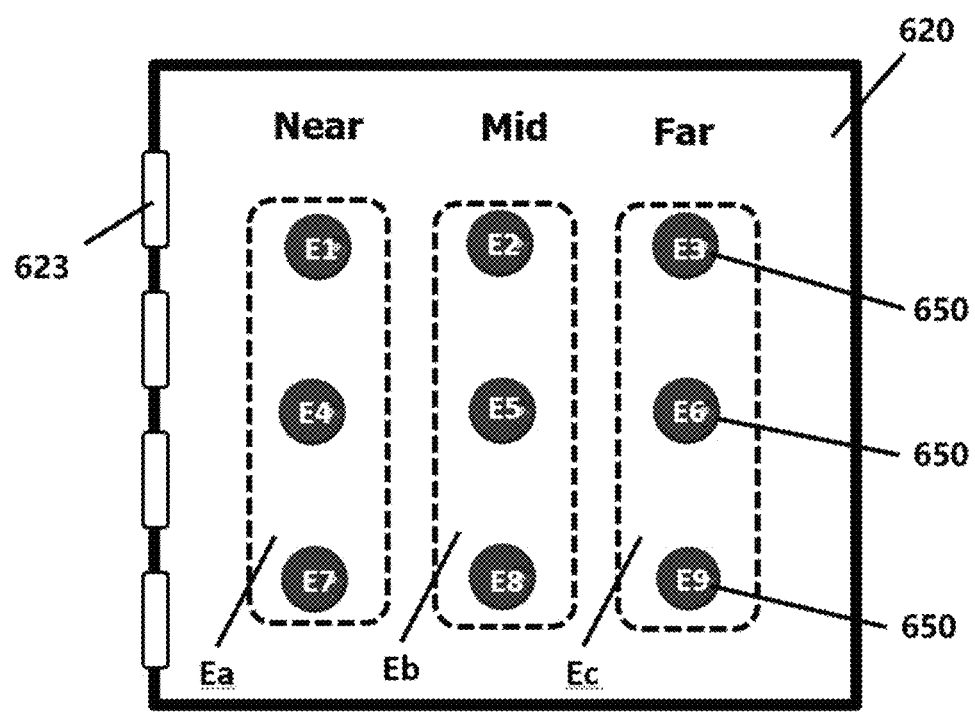

First, FIG. 10a shows that a plurality of ambient light sensors 650 are arranged at intervals in a space 620. In one embodiment, the distances between the plurality of ambient light sensors 650 are the same. In FIG. 10b and FIG. 10c, on the basis of FIG. 10a, a plurality of ambient light sensors 650 are arranged at intervals in the space 620 for grouping. Wherein, a preferred embodiment in FIG. 10b is to group a plurality of spaced ambient light sensors 650 in the horizontal direction (from the left side facing the direction shown in the figure to the right side). A preferred embodiment in FIG. 10c is to group a plurality of spaced apart ambient light sensors 650 in the vertical direction (from the top to the bottom facing the direction shown in the figure). The purpose of grouping is that when the area of the space 620 is large and the number of ambient light sensors 650 configured is large, after the ambient light sensors 650 are grouped first, the controller 670 can perform parallel calculation and control according to the number of groups, so as to reduce the load of the controller 670. In the embodiment shown in FIG. 10d, the space 620 is divided into a plurality of sub-spaces of different sizes by the spacer 625. Wherein, both the secondary space 6210 and the secondary space 6220 have windows to allow external light to enter the secondary space 6210 and the secondary space 6220, while the secondary space 6230 is a closed space that will not be affected by external light. Its purpose is to reveal and deduce the light environment of various specific environments.

Figure 11A:
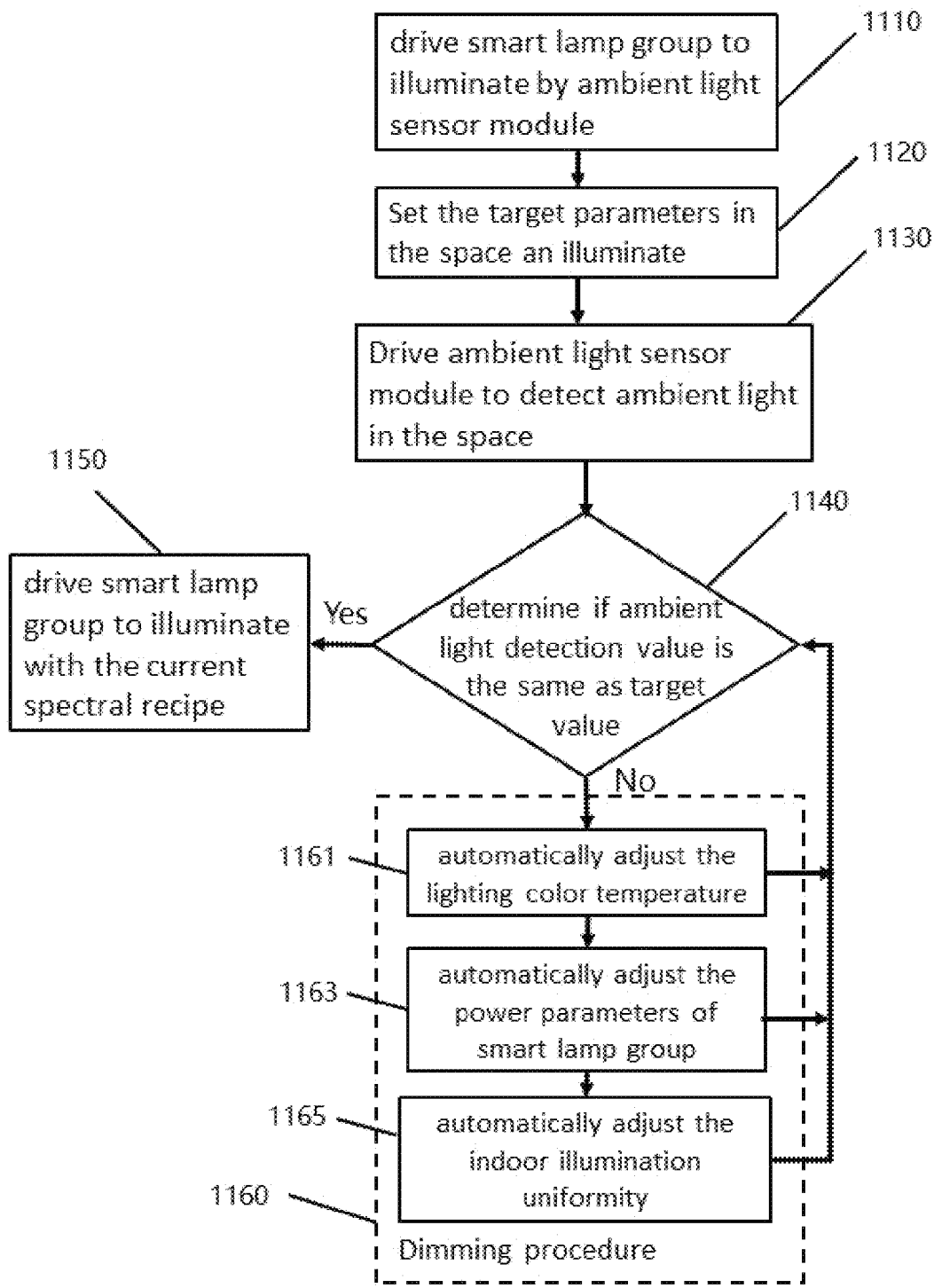
FIG. 11a is an intelligent method for automatically adjusting lighting parameters of the space according to the present invention.

Next, please refer to FIG. 11a, which is an intelligent method for automatically adjusting spatial lighting parameters according to the present invention. First, as shown in step 1110, the ambient light sensor module 650 drives the smart lamp group 621 in the space 20 to illuminate. The lighting parameter for lighting may be a preset light recipe. Wherein, the preset light recipe can be obtained from the control panel 670 by the ambient light sensor module 650. The preset lighting parameters of the light recipe may include information such as illuminance, CCT, color rendering (Ra), equivalent melanopic illuminance (EML), circadian action factor (CAF), light flicker frequency (Flicker) and/or illuminance uniformity.

Next, as shown in step 1120, the user sets the target lighting parameters in the space. In an embodiment of the present invention, the target lighting parameters may include illuminance, CCT, color rendering (Ra), equivalent melanopic illuminance (EML), circadian action factor (CAF) and/or illuminance uniformity. For example, when the user uses the control device 670 to set the "target parameters" of a work area to be 5700K CCT, illuminance and CAF=0.6, the ambient light sensor module 650 will drive the smart lamp group 621 according to the target lighting parameters of the "spectral recipe" of the work area illuminating is carried out.

Next, as shown in step 1130, the ambient light sensor module 650 is driven to detect the ambient light in the space 20. For example, the control device 670 drives the ambient light sensor module 650 to detect the ambient light of the light environment in the space 20. Wherein, driving the ambient light sensor module 650 detects the ambient light of the light environment in the space 20 through the light detection module configured therein, and the detected lighting parameters include at least illuminance (lx) and Correlated Color Temperature (CCT). Since the location of each driving ambient light sensor module 650 is different, the illuminance (lx) and Correlated Color Temperature (CCT) detected by each driving ambient light sensor module 650 will be different. In particular, when the field area of the space 20 is larger, the uneven illuminance caused by illuminance (lx) and Correlated Color Temperature (CCT) at different positions is more serious. For example, in FIG. 10a, the illuminance measured by the No. 1 ambient light sensor module=800 and the CCT=6200K, the illuminance measured by the No. 2 ambient light sensor module=400 and the CCT=5500K, and the illuminance measured by the No. 3 ambient light sensor module=100 and the CCT=5200K. It should be emphasized that the ambient light detection of the space 20 shown in step 1130 is performed continuously. Therefore, the value of the light parameters detected by the ambient light sensor module 650 will be recorded or stored and send to the memory of the control device 670 (not shown in the figure) according to the schedule.

Next, as shown in step 1140, it is compared and determined whether the ambient light detection value is the same as the target value. For example, the control device 670 compares the value of the light parameters detected by each driving ambient light sensor module 650 with the set target parameters. If the comparison result of the control device 670 is that the preset lighting parameter detected by the driving ambient light sensor module 650 is the same as the set target lighting parameter, then go to step 1150. For example, when the illuminance and Correlated Color Temperature (CCT) measured by No. 1, No. 2 and No. 3 ambient light sensor modules (6501, 6502, 6503) in FIG. 10*a* are all the same as the target parameters, then go to step 1150. The smart lamp group 621 is driven by the ambient light sensor module 650 to provide lighting with the current light parameters and stores them in the control device 670. In addition, if the comparison result of the control device 670 is that at least one preset lighting parameter detected by the driving ambient light sensor module 650 is not the same as the set target parameter, then go to step 1660. In step 1660, the control device 670 drive the ambient light sensor module to the smart lamp group to perform dimming procedures. As mentioned above, the ambient light sensor module 650 of the present invention is a sensor chip with constant illuminance, so it can continuously detect the changes of the lighting parameters in the space 620 and send them to the storage device during the working period of the chip.

In the present invention, the dimming procedure in step 1160 is divided into three steps for execution. First, as shown in step 1161, the ambient light sensor module 650 automatically adjusts the lighting CCT according to the target parameters. For example, when the CCT measured by the No. 1 ambient light sensor module is 6200K, the ambient light sensor module 650 will gradually adjust the illuminance provided by the paired smart lamp group 621 to 5700K. Similarly, the illuminance provided by the smart lamp group 621 paired with the ambient light sensor module No. 2 and the ambient light sensor module No. 3 is gradually adjusted to 5700K in sequence. It should be emphasized that, as shown in FIG. 10*a*, the worst case is when the CCT of the nine ambient light sensor modules are all different from the CCT set by the target parameters, the sequential or parallel processing is used to adjust the CCT of each ambient light sensor module to 5700K. The invention is not limited. The second step of the dimming procedure will not be performed until the control device 670 confirms that the CCT of each ambient light sensor module is adjusted to 5700K. The embodiment of the dimming procedure is illustrated by adjusting the CCT, and it is not intended to limit the dimming procedure of the present invention to only adjust the CCT. As mentioned above, the preset lighting parameters of the present invention can include illuminance, CCT, color rendering (Ra), equivalent melanism illuminance (EML), circadian action factor (CAF), light flicker frequency and/or illuminance uniformity, etc., all of which can be adjusted in the dimming procedure.

The second step, as shown in step 1163, is to automatically adjust the power parameters of the smart lamp group 621. The control device 670 controls the power value of the paired smart lamps 621 according to the location of the ambient light sensor module 650. In this embodiment, the power of the smart lamp group 621 is controlled by pulse-width modulation (PWM). For example, the No. 1 ambient light sensor module 6501 is the closest to the window, so its background light is the brightest, so a lower power value can be given. For example, the PWM of the smart lamp group 621 paired with the No. 1 ambient light sensor module 6501 is provided with a duty cycle of 30%. For example, according to the position of the No. 2 ambient light sensor module 6502 from the window, it is possible to provide a duty cycle of 50% PWM of the smart lamp group 621 paired with the No. 2 ambient light sensor module 6502. For example, since No. 3 ambient light sensor module 6503 is the farthest away from the window, it is possible to provide a PWM duty cycle of 80% for the smart lamp group 621 paired with No. 3 ambient light sensor module 6503. Obviously, the present invention uses PWM dimming because PWM dimming has the advantages of no color shift, high dimming precision, combined with digital technology dimming, wide dimming range, and no flicker. In addition, after passing this step, energy saving requirements can also be met.

The third step, as shown in step 1165, is to automatically adjust the uniformity ratio of indoor illumination. According to the actual illuminance detected by the ambient light sensor module 650, after the calculation of the illuminance uniformity formula, compared with the target illuminance uniformity, if the illuminance uniformity has reached the target value, go to step 1150. Step 1150 provides lighting with current lighting parameters and stores them in control device 670. Wherein, the calculation formula and case of illuminance uniformity are explained as the following equation 1.

$$\text{illuminance uniformity} = \text{minimum illuminance/average luminance} \quad \text{(equation 1)}$$

For example, when the target illuminance uniformity is set to 0.6, the illuminance measured by No. 1, No. 2 and No. 3 ambient light sensor modules in FIG. 10*a* are 800, 400 and 100 respectively. Then the average illuminance value measured by No. 1, No. 2 and No. 3 ambient light sensor modules is $(800+400+100)/3=433$, then according to equation 1 can be obtained the illuminance uniformity$=100/433=0.23$.

After illuminating, the illuminance uniformity obtained by No. 1, No. 2 and No. 3 ambient light sensor modules in FIG. 10*a* is 0.23. Obviously, the set value of the target illuminance uniformity of 0.6 has not been reached. Therefore, it is necessary to adjust the illuminance of the smart lamp group 621 paired with the No. 1, No. 2 and No. 3 ambient light sensor modules. In a preferred embodiment of the present invention, when the actual illuminance uniformity is lower than the target illuminance uniformity, the intelligent lamp group 621 with the minimum illuminance (that is, the smart lamp group 6503 farthest from the window) is prioritized for adjustment. For example, the control device 670 drives the intelligent lamp group 621 paired with the ambient light sensor module No. 3 to increase its illuminance. For example, when the illuminance of No. 3 smart lamp group 621 is increased to 300, the average illuminance value measured by No. 1, No. 2 and No. 3 ambient light sensor modules is $(800+400+300)/3=500$, then according to equation 1 can be obtained the illuminance uniformity$=300/500=0.6$.

When the adjusted illuminance uniformity has reached the target illuminance uniformity, go to step 1150 to provide illumination with the current lighting parameters and store it in the memory.

Next, it should be further explained that after illuminating, the real illuminance uniformity of the 9 ambient light sensor modules in FIG. 10*a* should be calculated by bringing the measured illuminance of the 9 ambient light sensor modules into Equation 1. For the 9 ambient light sensor modules shown in FIG. 10b, 9 ambient light sensor modules are divided into groups according to the space 20, the average illuminance of each zone (Ea, Eb, Ec) is firstly calculated. For example, as shown in the following.

$$Ea=(E1+E2+E3)/3$$

$$Eb=(E4+E5+E6)/3$$

$$Ec=(E7+E8+E9)/3$$

Then, the illuminance uniformity in FIG. 10b is obtained according to equation 1, wherein the calculation is as the following equation 2.

illuminance uniformity=Min($Ea,Eb,Ec$)/Avg($Ea,Eb,Ec$)     (equation 2)

Finally, determine whether the illuminance uniformity in the FIG. 10b is greater than the set target value.

For the 9 ambient light sensor modules shown in FIG. 10c, the average illuminance of each zone (Ea, Eb, Ec) is firstly calculated. For example, as shown in the following.

$$Ea=(E1+E4+E7)/3$$

$$Eb=(E2+E5+E8)/3$$

$$Ec=(E3+E6+E9)/3$$

Then, since the distances of Ea, Eb, and Ec relative to the opening 623 are different, some weight distribution needs to be given the illuminance uniformity in FIG. 10c is obtained according to equation 1, where the calculation is as the following equation 3.

illuminance uniformity 7 Min($Ca*Ea,Cb*Eb,Cc*Ec$)/Avg($Ca*Ea,Cb*Eb,Cc*Ec$)     (equation 3)

Wherein, Ca, Cb, Cc, are the parameters of weight, for example, in the embodiment of the present invention, the parameter of weight can be Ca is between 0.25~0.5, Cb is between 0.5~0.75, and Cc is between 0.75~1.0.

Finally, determine whether the illuminance uniformity in the FIG. 10c is greater than the set target value.

Figure 10D:
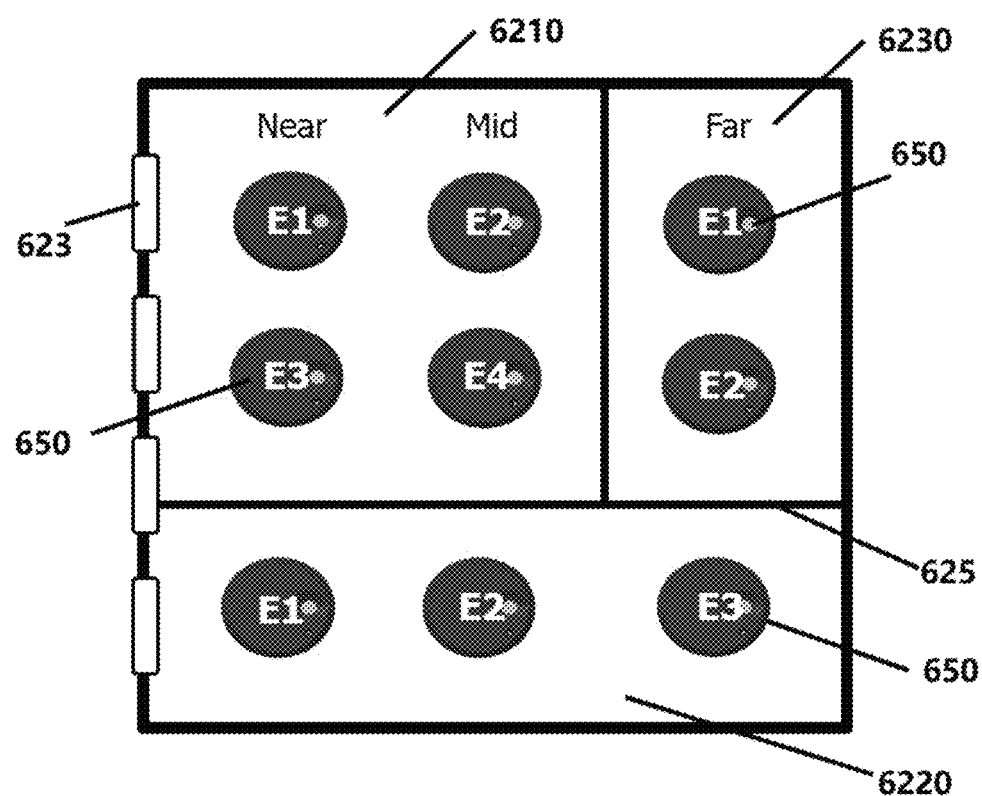

Further, in the embodiment of FIG. 10d, multiple sub-spaces of different sizes can be distinguished in space 620, but all of them can be calculated according to equation 1 in FIG. 10c. Finally, when the present invention completes the dimming procedure in step 1160 and compares the dimmed lighting parameters in step 1140 and confirms that they meet the target parameters, it will proceed to step 1150. The ambient light sensor module 650 continues to drive the smart lamp group 621 to provide lighting with the current (and after dimming) lighting parameters and store the current lighting parameters in the control panel 670.

In addition, it should be emphasized that in the dimming procedure in step 1160 of the present invention, step 1163 of automatically adjust the power parameter of smart lamp group 621 can be optionally added to the dimming procedure. When both step 1163 and step 1165 are implemented, it will be another preferred embodiment of the present invention. And if the illuminance of the target parameter includes information such as equivalent melanopic illuminance (EML) and circadian action factor (CAF), the equivalent melanopic illuminance (EML) and circadian action factor (CAF) can be obtained by calculation according to the illuminance detected by the ambient light sensor 650.

Figure 11B:
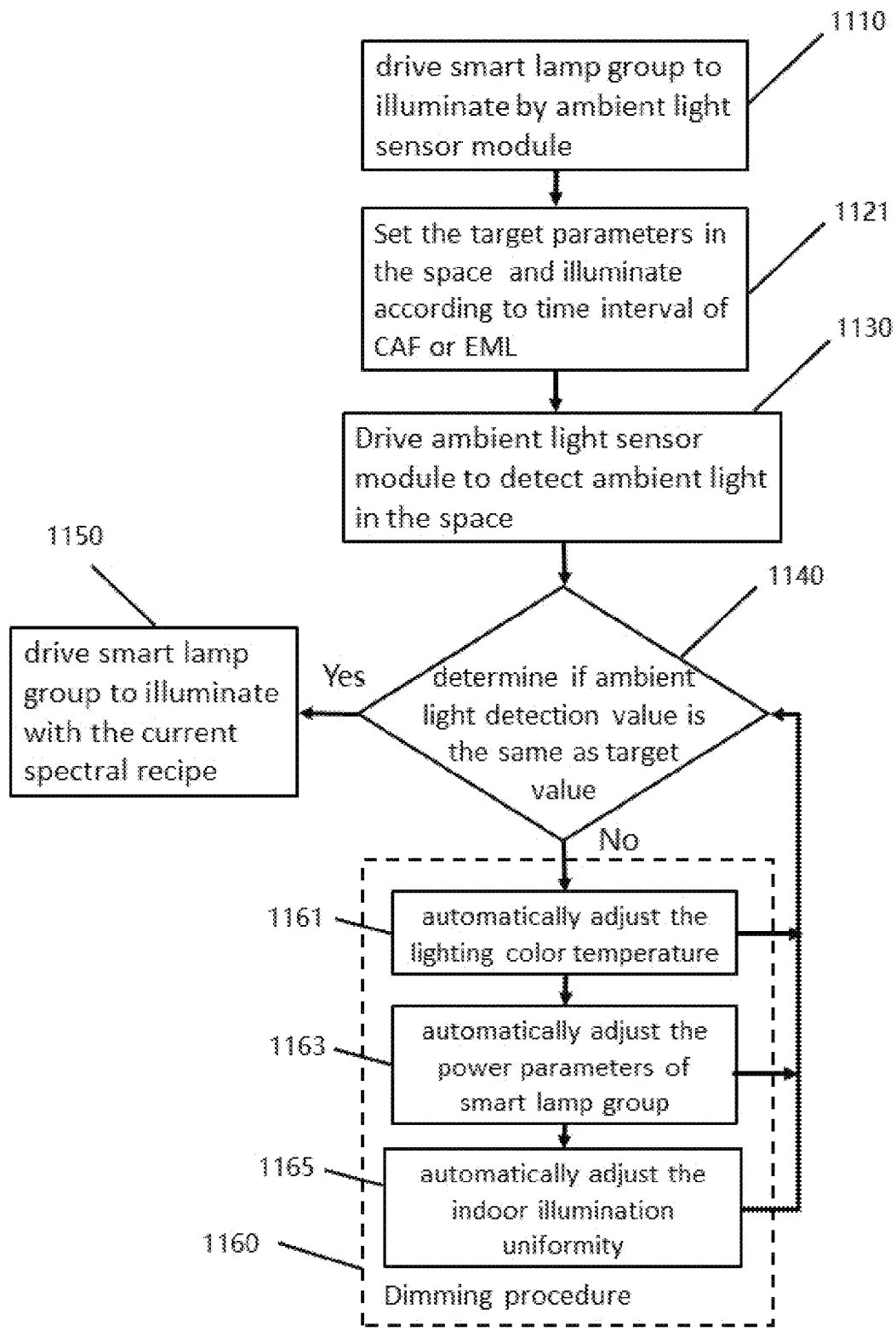
FIG. 11b is another intelligent method for automatically adjusting lighting parameters of the space according to the present invention.

Next, please refer to FIG. 11b, it is another smart method for automatically adjusting spatial lighting parameters according to the present invention. In particular, the difference between FIG. 11 b and FIG. 11 is in step 1121. As shown in step 1121, the control device 670 can set value such as equivalent melanopic illuminance (EML) and circadian action factor (CAF) related to the circadian rhythm (Circadian) of the human body as the target parameters set in the space 620 according to the interval of the daily time. The difference between CAF and EML is that CAF measures the stimulation of the light spectrum of the intelligent lamp group 621 on the human body, while EML measures the stimulation of the field on the human body. But the same thing is that the higher the value, the higher the stimulation to the human body can boost the spirit, the lower the value, the lower the stimulation to the human body is to help relax the body and mind. For example, keep CAF>0.4 during people's daytime activity time, and keep CAF<0.1 after dusk. As far as EML is concerned, the WELL building standard requires that the EML of the human body should reach 200-250 during daytime activities, and the EML should be lower than 50 after entering dusk. Therefore, the present invention can use equivalent melanopic illuminance (EML) and circadian action factor (CAF) as one of target parameters.

In a preferred embodiment, in step 1125, a value database of CAF or EML parameter can be established, and the CAF or EML target parameters in step 1121 can be automatically replaced according to the time interval. Next, as shown in FIG. 11b, after updating the CAF or EML target parameters, steps from step 1130 to step 1165 are the same as the corresponding steps in FIG. 11a.

For example, in the interval between 9 and 11 in the morning, the present intelligent human centric lighting system can already provide the physiological target parameters of this time interval, especially the target parameters whose CCT is adjusted to 5700K, CAF value is greater than 0.4, and EML reaches 0.65. Then, when the time interval enters the interval from 11 to 13 o'clock, according to step 1125, establish a new parameter database such as CCT, CAF or EML. For example, the target parameters set are CCT=4000K, illuminance uniformity=0.51, and CAF maintenance is greater than 0.4 and EML maintained at 200. At this time, in step 1121, the control device 670 drives the ambient light sensor 650 to illuminate according to the newly set target parameters. Then, go to step 1130. In step 1130, the light in the space 20 is detected by the ambient light sensor 650, and in step 1140, the detected light parameters are compared with the newly set target parameters. Obviously, since the target parameter has been changed to a newly set target parameter, it is necessary to enter into the dimming procedure of step 116. At this time, as shown in step 1161, the ambient light sensor module 650 firstly gradually adjusts the illuminance provided by the paired smart lamp group 621 to 4000K. When the control device 670 confirms that the CCT of each smart lamp group 621 has been adjusted to 4000K, the procedure of step 1163 will be performed to appropriately adjust power parameters of the smart lamp group 621 according to the location of the ambient light sensor module 650. Then, go to step 1165, which is to automatically adjust the uniformity of indoor illuminance. Similarly, according to the illuminance detected by the ambient light sensor module 650, it is calculated by the illuminance uniformity formula and compared with the target illuminance uniformity. If the illuminance uniformity has reached the target value, go to step 1150 to provide illumination with the current light parameters and store it in the memory. For example, when the illuminance of No. 1 smart lamp group 621 is reduced to 250, the average illuminance value measured by No. 1, No. 2 and No. 3 ambient light sensor modules is (800+400+

250)/3=483, then according to equation 1 can be obtained illumination uniformity=250/483=0.52.

When the adjusted illuminance uniformity has reached the standard illuminance uniformity, go to step 1150, provide illumination with the current light parameters and store it in the memory.

Afterwards, when the time interval is changed, step 1125 will update the target parameters in step 1121 again according to the parameter database such as CCT, CAF or EML, and then repeat steps 1130 to 1165, so that the present invention provides an automatic adjustment Intelligent human centric lighting system with spatial lighting parameters.

Finally, it should be emphasized once that the above is only a better embodiment of the present invention and is not used to limit the scope of the rights of the present invention. At the same time, the above description should be clear to and implemented by those with general knowledge in the relevant technical field. Therefore, other equivalent changes or modifications not separated from the concept disclosed in the present invention should be included in the scope of patent claims of the present invention.

What is claimed is:

1. A method for automatically adjusting the lighting parameters of a space, wherein a plurality of smart lamp groups, a plurality of ambient light sensor modules, a control module, and an interface device are arranged in the space and are connected through a wireless communication protocol; the smart lamp group and the interface device are respectively paired to the ambient light sensor module and the control module through the wireless communication protocol; and the control module and interface device are connected to the cloud through the Artificial Intelligence of Things, the method comprising the following steps:
    driving the smart lamp groups to illuminate in the space, wherein the ambient light sensor module drives the smart lamp groups to illuminate in the space by using the lighting parameters of the preset light recipe;
    setting the target lighting parameters in the space, wherein the control module sets the equivalent melanopic illuminance (EML) and circadian action factor (CAF) of the human circadian rhythm according to the interval of the daily time, as the target lighting parameters in the space;
    driving the ambient light sensor modules to perform an ambient light detection in the space by the control module and sending the ambient light detection value to the control module; and
    determining if the ambient light detection value is the same as the value of the target lighting parameters, wherein the control module compares the ambient light detection value in the actual environment with the value of the target lighting parameters, wherein
    when it is determined that the ambient light detection value is the same as the value of the target lighting parameters, the ambient light sensor module continues to drive the smart lamp groups to illuminate with the lighting parameters of the preset light recipe; and
    when it is determined that the ambient light detection value is not the same as the value of the target lighting parameters, the control module drives the ambient light sensor module performs a dimming procedure to the smart lamp groups, wherein the dimming procedure comprising the following steps:
    performing the dimming procedure according to the target lighting parameters by the ambient light sensor module, so that the value of the lighting parameter in the actual environment is the same as the value of the set target lighting parameters; and
    adjusting an illuminance uniformity of the space according to the actual illuminance detected by the ambient light sensor module, after the calculation of the illuminance uniformity formula, the illuminance uniformity is adjusted to be the same as a target illuminance uniformity.

2. The method according to claim 1, wherein the interface device is paired with the ambient light sensor module and the control module through a software-as-a-service (SaaS) or platform-as-a-service (PaaS) system program.

3. The method according to claim 1, wherein the lighting parameters of the preset light recipe includes illuminance, Correlated Color Temperature (CCT), color rendering (Ra), equivalent melanism illuminance (EML), circadian action factor (CAF), light flicker frequency and/or illuminance uniformity.

4. The method according to claim 3, further comprising the step of establishing a numerical database of CAF or EML parameters, and automatically replace CAF or EML target parameters according to the time interval.

5. The method according to claim 1, wherein when it is determined that the ambient light detection value is the same as the value of the target lighting parameters, further includes a step to adjust the power parameters of the smart lamp group to control the power value of the paired smart lamp group by the control module according to the location of the ambient light sensor module.

6. The method according to claim 5, wherein adjusting the power parameters of the smart lamp group is to control the power of the smart lamp group by pulse width modulation (PWM).

7. The method according to claim 1, wherein the formula for illuminance uniformity is as the following equation 1, $$\text{luminance uniformity} = \text{minimum illuminance/average luminance} \quad \text{(equation 1)}.$$

8. A system for automatically adjusting the lighting parameters of a space, the system includes a plurality of smart lamp groups, a plurality of ambient light sensor modules, a control module, and an interface device arranged in the space and are connected through a wireless communication protocol, and the smart lamp group and the interface device are respectively paired to the ambient light sensor module and the control module through the wireless communication protocol, the system comprising:
    the control module sets the target lighting parameters in the space and drive the smart lamp groups to illuminate by using the lighting parameters of the preset light recipe and to control the smart lamp groups to perform the illumination, wherein the lighting parameters of the preset light recipe includes illuminance, CCT, color rendering (Ra), equivalent melanism illuminance (EML), circadian action factor (CAF), light flicker frequency and/or illuminance uniformity and the control module establishes a numerical database of CAF or EML parameters, and automatically replace CAF or EML target parameters according to the time interval;
    the control module compares an ambient light detection value in the actual environment with the value of the target lighting parameters, wherein
    when it is determined that the ambient light detection value is the same as the value of the target lighting parameters, the ambient light sensor module continues to drive the smart lamp groups to illuminate with the lighting parameters of the preset light recipe; and when it is determined that the ambient light detection value is not the same as the value of the target lighting parameters, the control module drives the ambient light sensor module performs a dimming procedure to the smart lamp groups, wherein the dimming procedure comprising the following steps:

performing the dimming procedure according to the target lighting parameters by the ambient light sensor module, so that the value of the lighting parameter in the actual environment is the same as the value of the set target lighting parameters; and adjusting an illuminance uniformity of the space according to the actual illuminance detected by the ambient light sensor module, after the calculation of the illuminance uniformity formula, the illuminance uniformity is adjusted to be the same as a target illuminance uniformity.

9. The system according to claim 8, wherein the interface device is paired with the ambient light sensor module and the control module through a software-as-a-service (SaaS) or platform-as-a-service (PaaS) system program.

10. The system according to claim 8, wherein when it is determined that the ambient light detection value is the same as the value of the target lighting parameters, further includes a step to adjust the power parameters of the smart lamp group to control the power value of the paired smart lamp group by the control module according to the location of the ambient light sensor module.

11. The system according to claim 10, wherein adjusting the power parameters of the smart lamp group is to control the power of the smart lamp group by pulse width modulation (PWM).

12. The system according to claim 8, wherein the formula for illuminance uniformity is as the following equation 1, $$\text{luminance uniformity} = \text{minimum illuminance/average luminance} \qquad \text{(equation 1)}.$$

* * * * *